United States Patent [19]

Lindauer

[11] Patent Number: 5,180,107
[45] Date of Patent: Jan. 19, 1993

[54] DISPENSING UNIT OF VOLATILIZABLE SUBSTANCE CAPABLE OF VISIBLE DETERMINATION OF ITS EXTENT OF USE

[75] Inventor: Jerome I. Lindauer, Hillsdale, N.J.

[73] Assignee: International Flavors & Fragrances Inc., New York, N.Y.

[21] Appl. No.: 789,680

[22] Filed: Nov. 8, 1991

[51] Int. Cl.$^5$ .............................................. A61L 9/00
[52] U.S. Cl. ...................................... 239/35; 239/55; 239/58
[58] Field of Search .................. 239/71, 74, 35, 34, 239/53–56, 58–59, 60

[56] References Cited

U.S. PATENT DOCUMENTS

| | | | |
|---|---|---|---|
| 2,251,058 | 7/1941 | Kirkman | 239/35 |
| 2,642,310 | 6/1953 | Meek et al. | 239/35 |
| 2,942,786 | 6/1960 | Wenner et al. | 239/35 |
| 3,104,816 | 9/1963 | Jaffe | 239/35 |
| 3,805,995 | 4/1974 | Lebel et al. | 220/70 |
| 3,964,684 | 6/1976 | Schimanski et al. | 239/56 |
| 4,258,004 | 3/1981 | Valenzona et al. | 422/123 |

FOREIGN PATENT DOCUMENTS 79044  6/1952  Norway ............................. 239/35

Primary Examiner—Andres Kashnikow
Assistant Examiner—Kevin Weldon
Attorney, Agent, or Firm—Arthur L. Liberman

[57] ABSTRACT

Described is a dispensing unit of a volatilizable substance capable of visible determination of its extent of use. The unit has a variably located centroid initially positioned proximate the geometric center point of the unit with the centroid moving downward when the unit is in use. As the volatilizable substance evaporates, a weight eccentrically located in the same place as the volatilizable substance angularly rotates about the "z" axis leaving its upper position and finally coming to rest at a lower position when the volatilizable material is used up. At least the final position is rendered visibly detectable by means of a simple sighting mechanism.

1 Claim, 15 Drawing Sheets

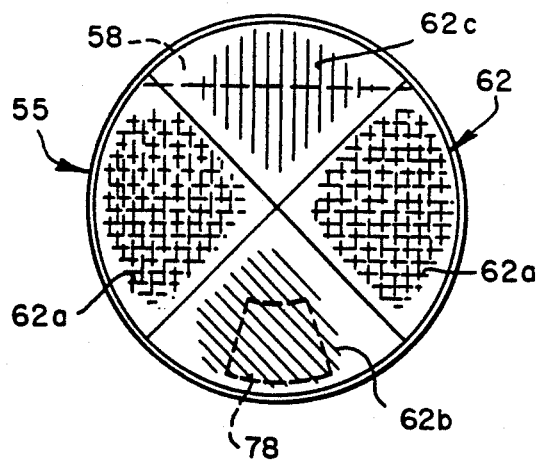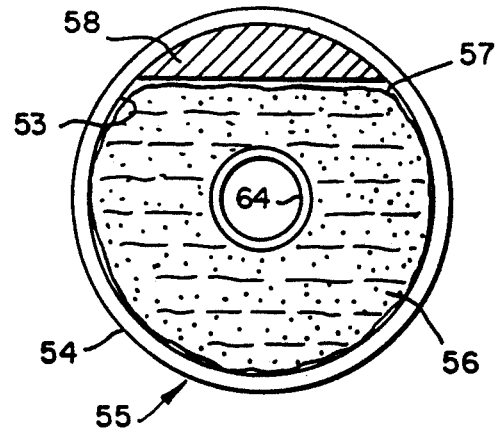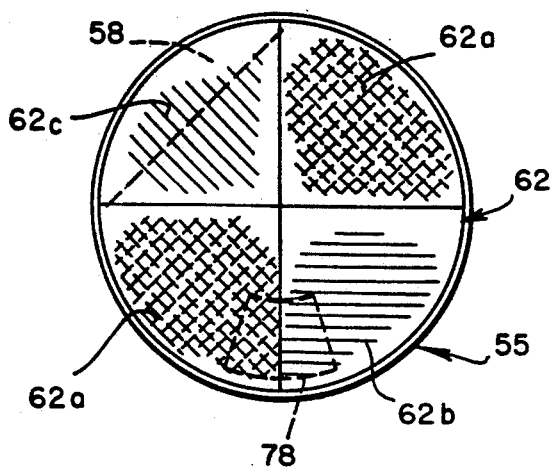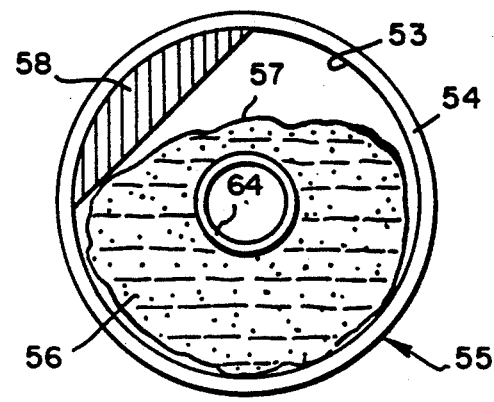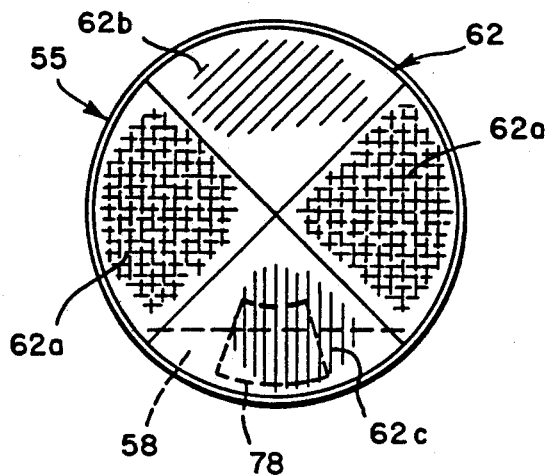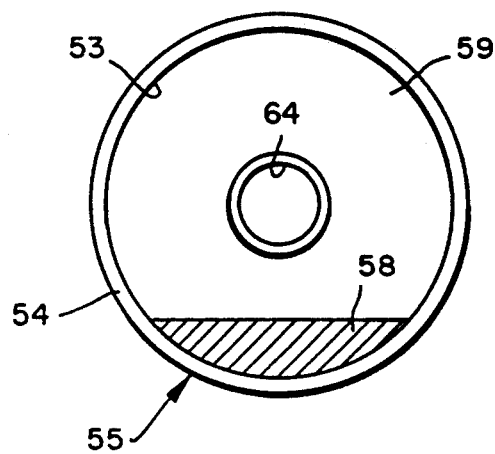

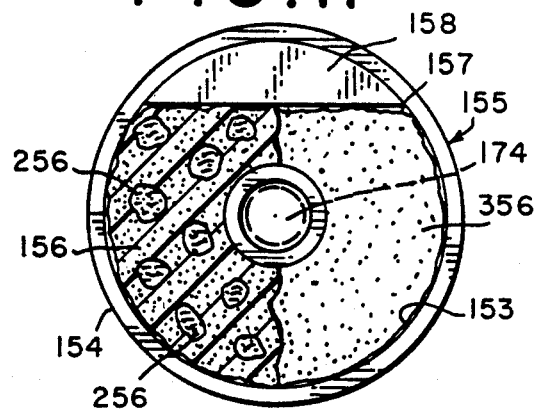
FIG.11
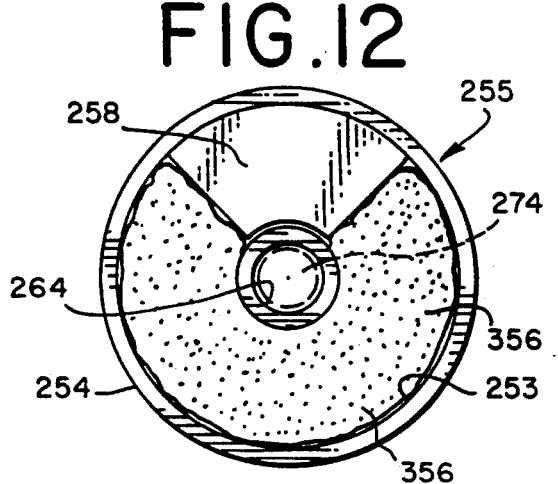
FIG.12
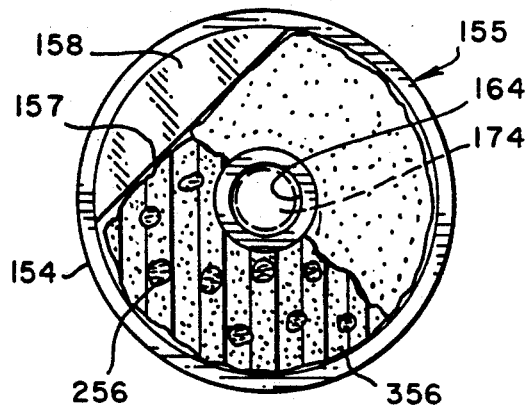
FIG.11-A
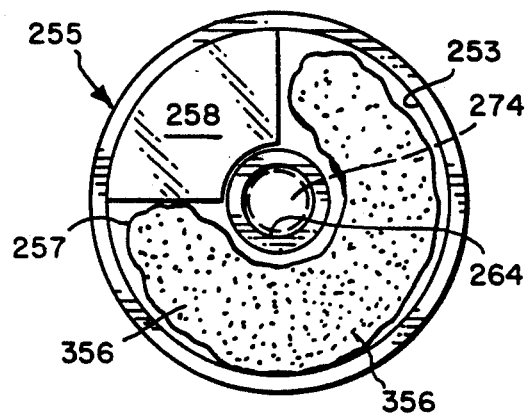
FIG.12-A
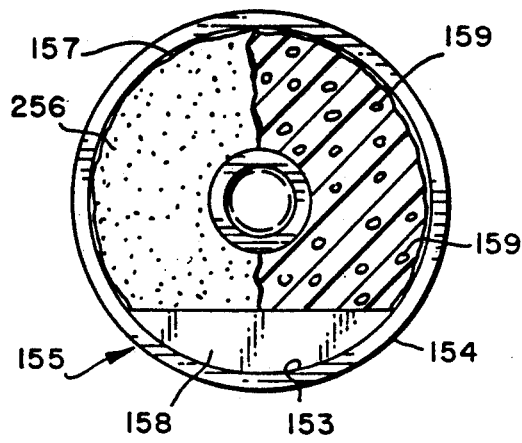
FIG.11-B
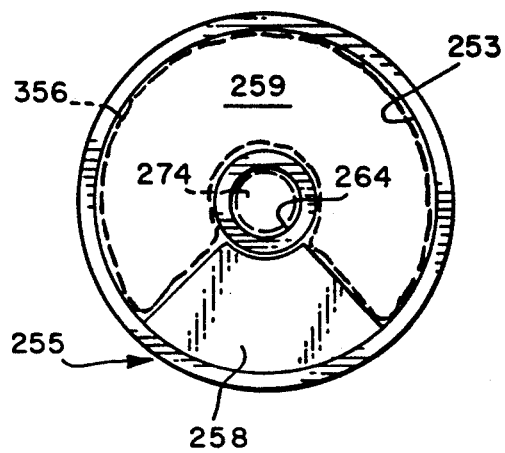
FIG.12-B

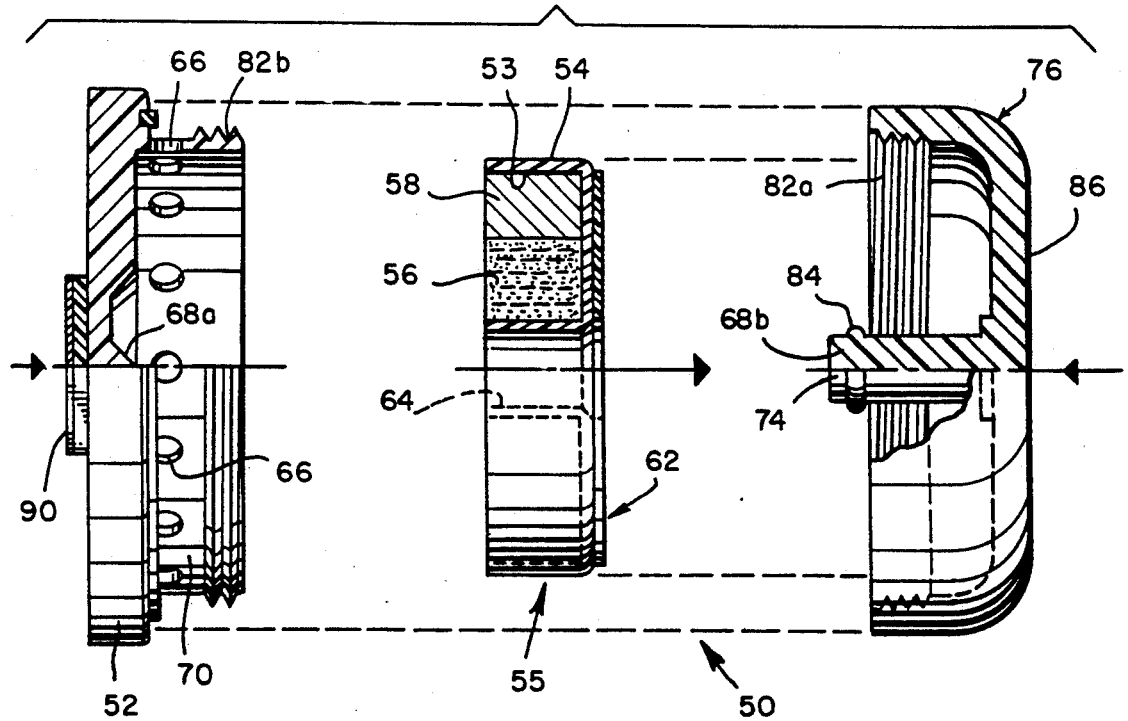

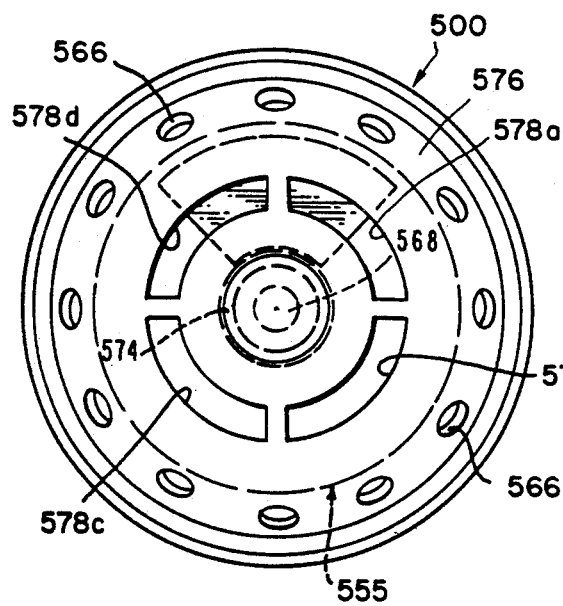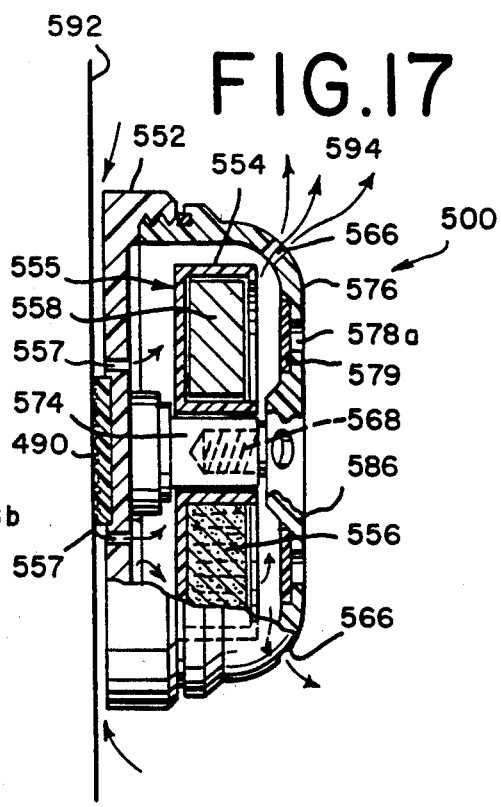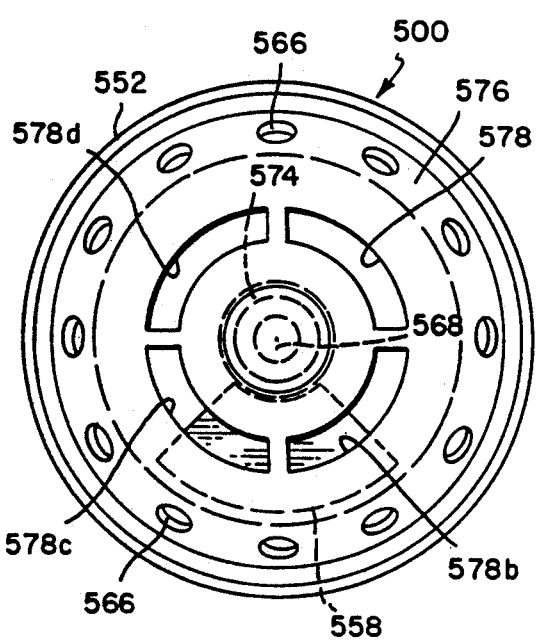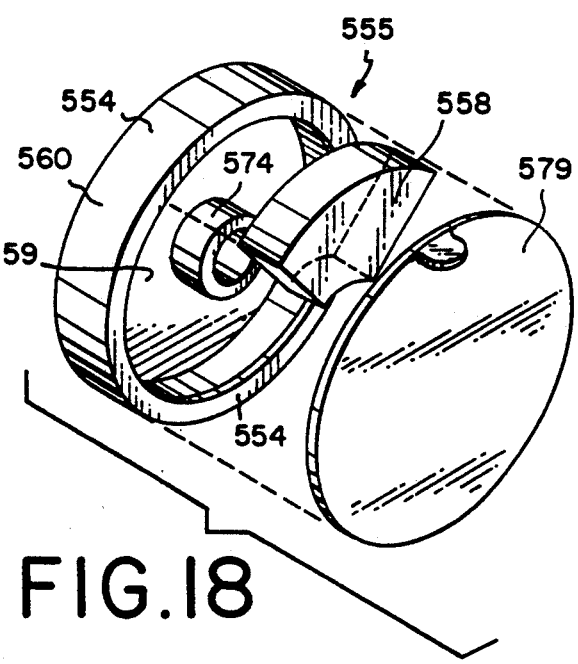

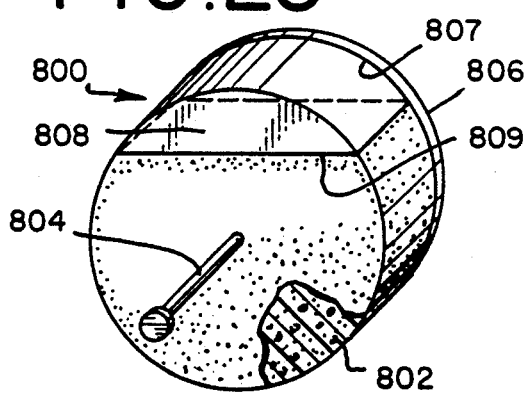
FIG.23
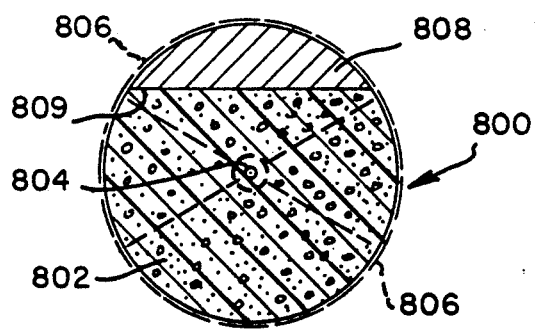
FIG.23-A
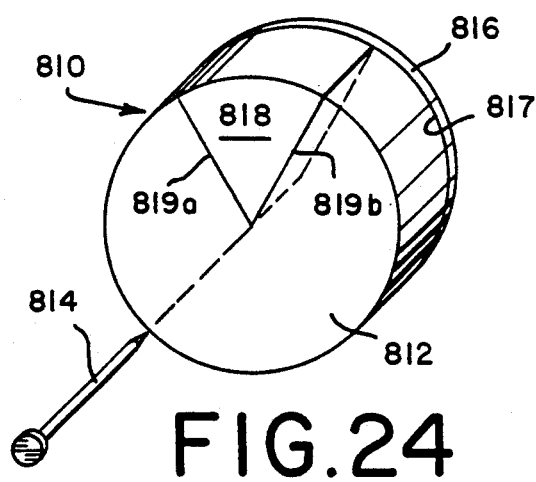
FIG.24
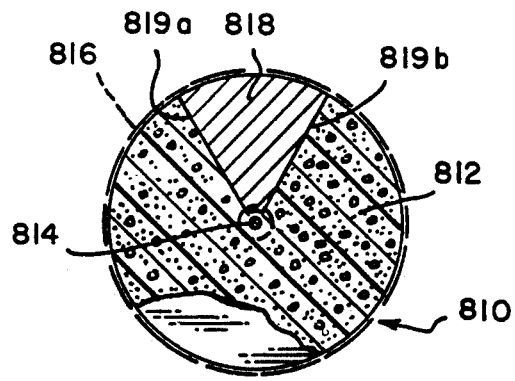
FIG.24-A
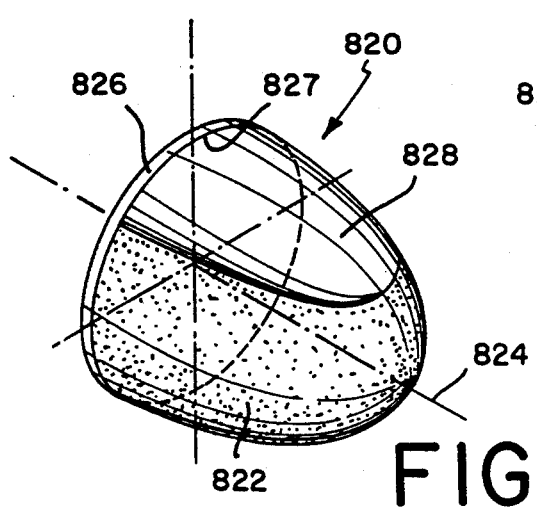
FIG.25
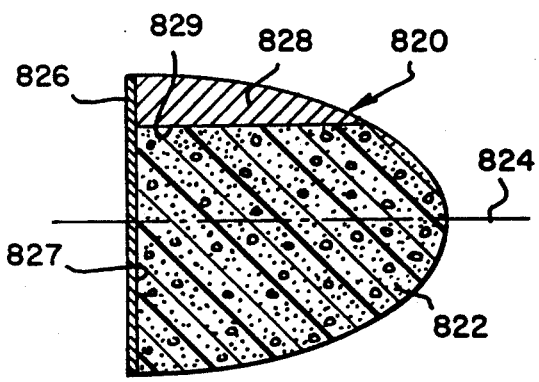
FIG.25-A

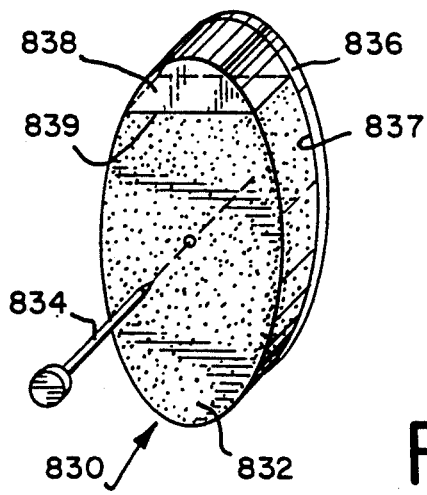
FIG.26
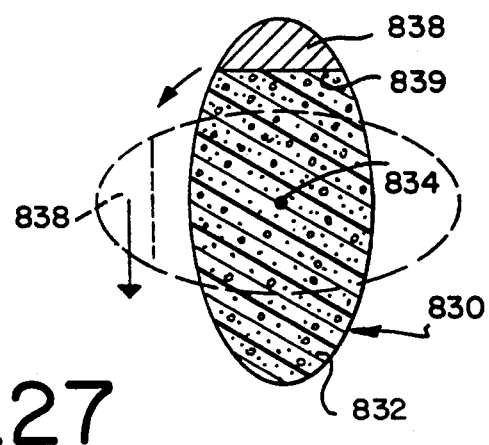
FIG.26-A
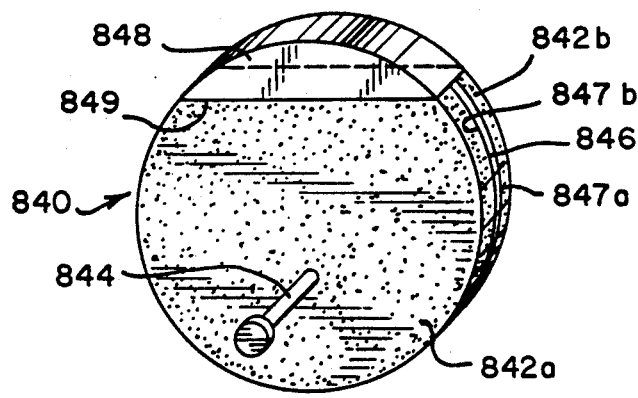
FIG.27
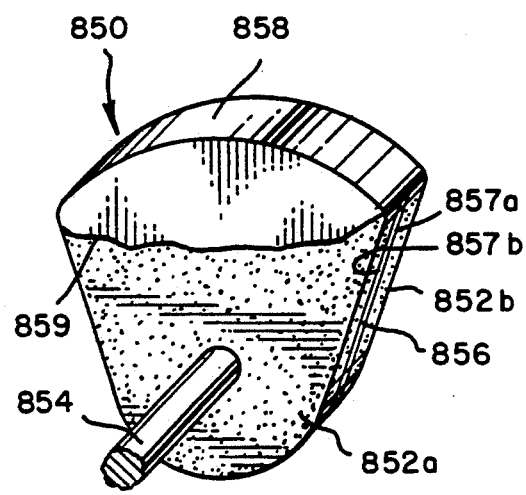
FIG.28
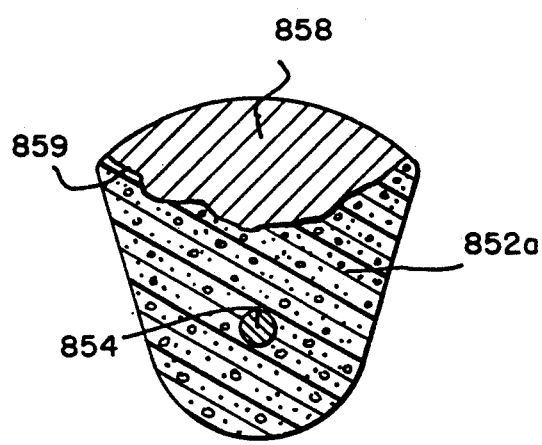
FIG.28-A FIG. 29
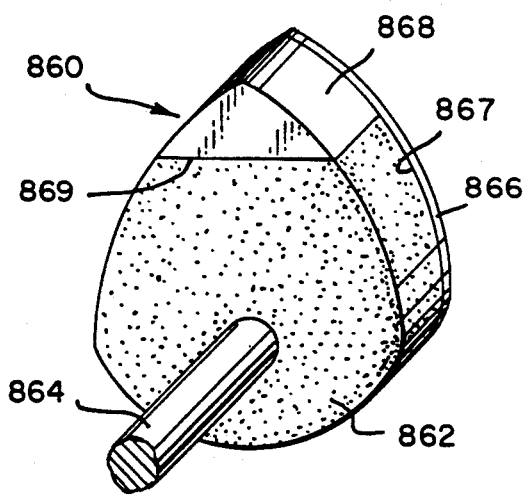
FIG. 29-A
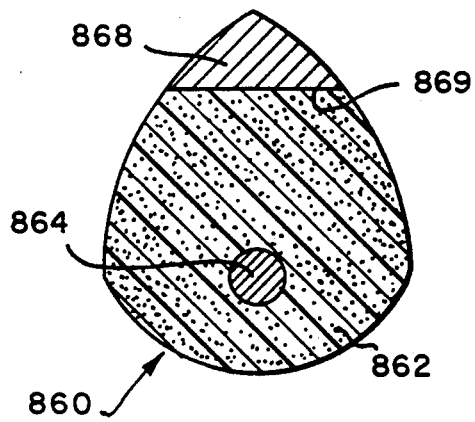
FIG. 30
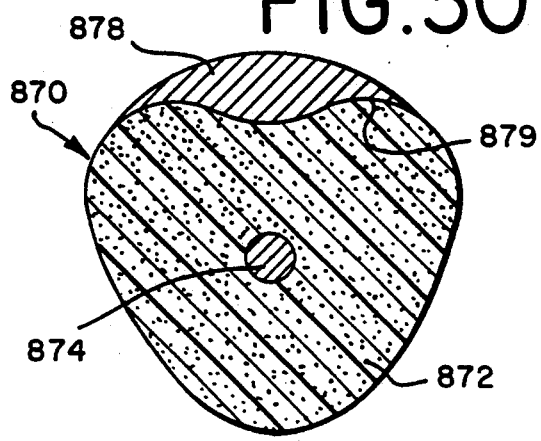
FIG. 31
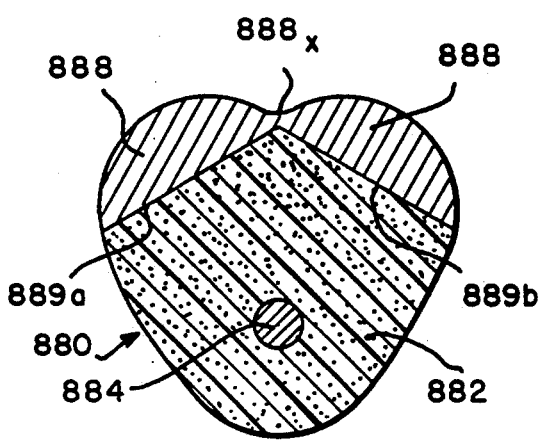
FIG. 32
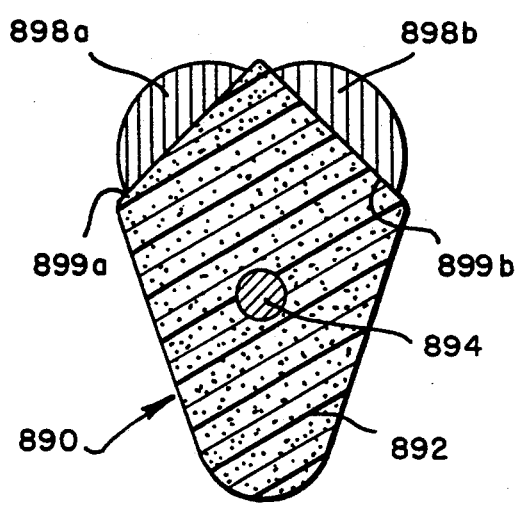
FIG. 33
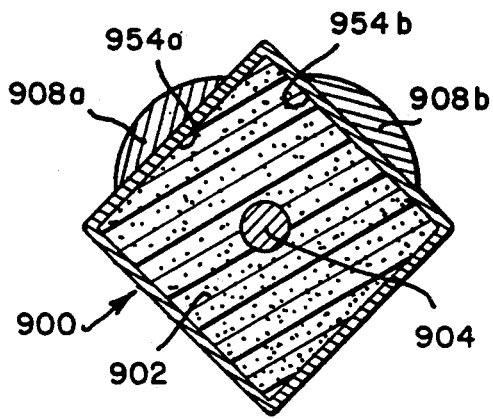

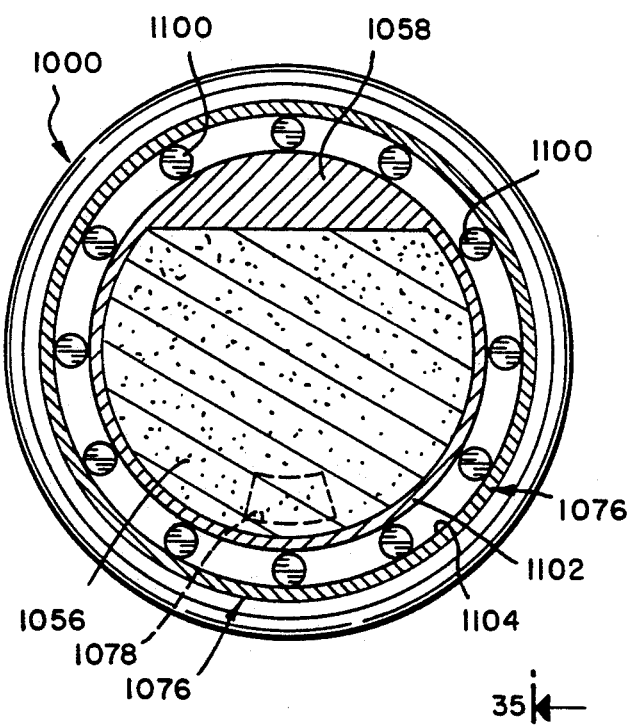
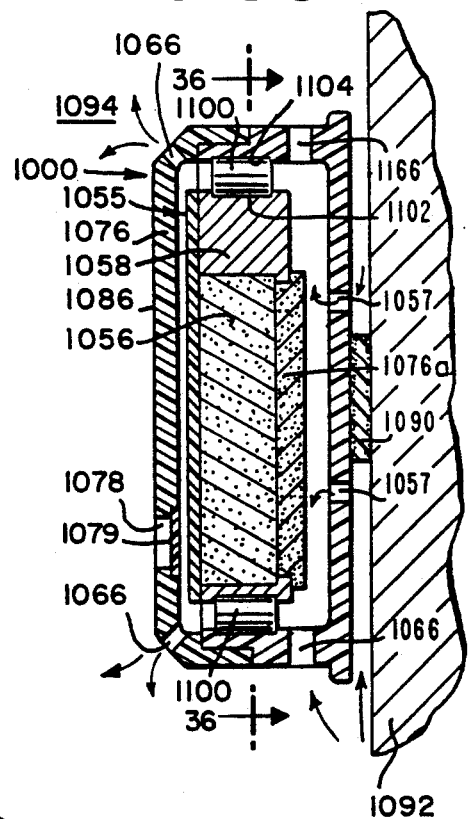
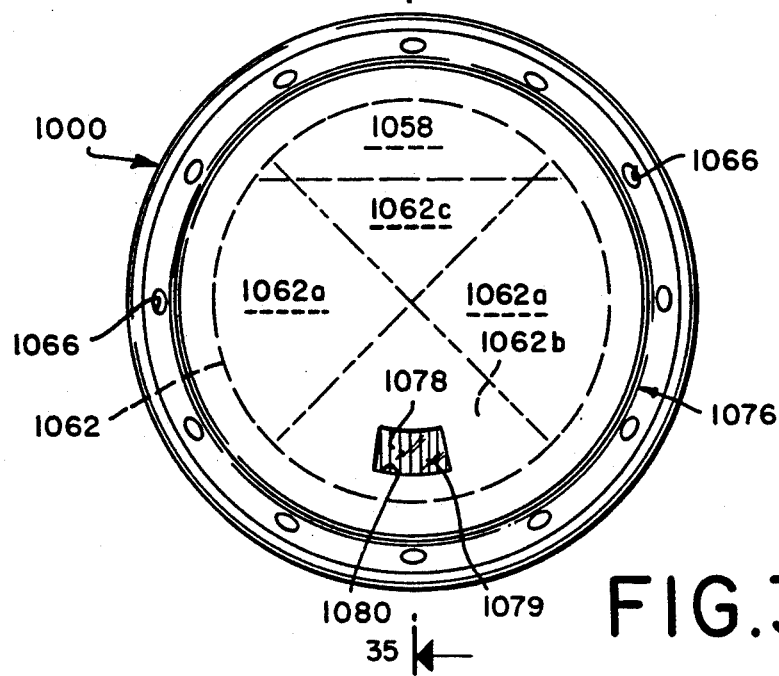

FIG.38
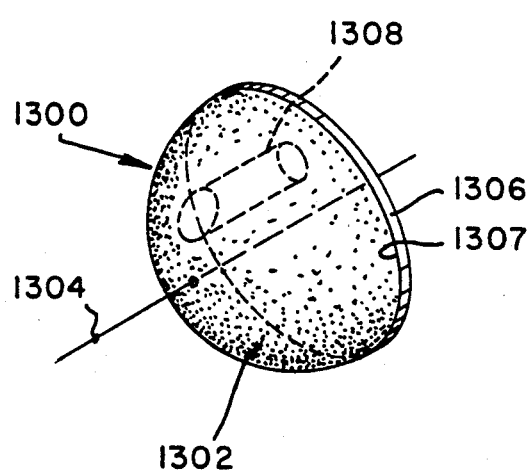
FIG.38-A
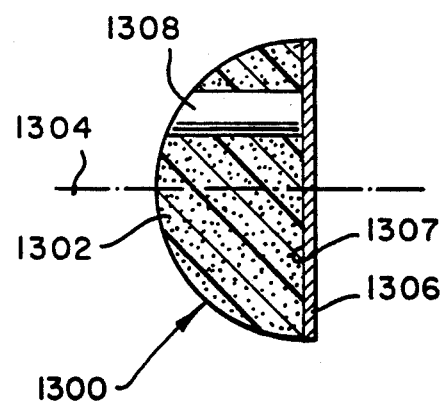
FIG.39
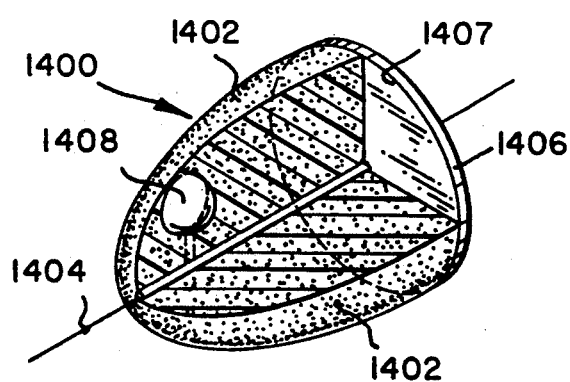
FIG.39-A
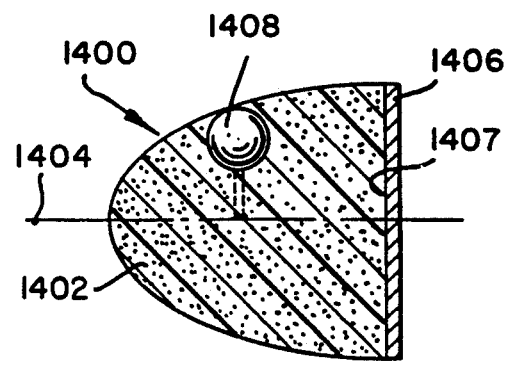

DISPENSING UNIT OF VOLATILIZABLE SUBSTANCE CAPABLE OF VISIBLE DETERMINATION OF ITS EXTENT OF USE

BACKGROUND OF THE INVENTION

My invention is a dispensing unit of a volatilizable substance such as a perfumery material, an insect repellent and an animal repellent or the like capable of visible determination of its extent of use comprising a sighting mechanism having associated therewith a vertically positioned rotatable support having located thereon in the same plane at least one gravity activated weight and a volatilizable substance and having a variably located centroid initially positioned proximate the geometric center point of the unit with the centroid moving downward when the unit is in use whereby as the volatilizable substance evaporates, the weight eccentrically located in the same plane as the volatilizable substance angularly rotates about the "z" axis leaving its initial position and finally coming to rest at a resting position while the volatilizable material is used up and whereby at least the final position of the weight is rendered visibly detectable by means of said sighting mechanism.

Dispensing units of volatilizable substances capable of visible determination of their extent of use are known in the prior art.

Thus, U.S. Pat. No. 2,642,310 issued on Jun. 16, 1953 entitled "Diffuser And Binder Base For Residue Of Evaporable Material" discloses and claims a dispensing unit of volatilizable material containing minor portions of non-volatilizing residue forming components, comprising a relatively flat receptacle having an enlarged bottom wall, a low peripheral side wall, and being open at the top thereof, said bottom wall having a thin sheet of fibrous material arranged along and in close proximity thereto, the surface of said sheet of fibrous material being adherent to the volatilizable material and providing means for adhering bodies of said non-volatilizable residue in fixed position with respect to said receptacle, with the sheet being characterized to function as a replacement indicator as portions thereof become exposed through evaporation of volatilizable material from the receptacle.

Articles which can be modified using weight means and sighting means which are dispensing units of volatilizable substance, but which are not disclosed to be so capable of being modified are set forth in U.S. Pat. No. 3,964,684 issued on Jun. 22, 1976 and U.S. Pat. No. 4,258,004 issued on Mar. 24, 1981. The disclosures of said U.S. Pat. Nos. 3,964,684 and 4,258,004 are incorporated herein by reference.

The prior art does not however disclose a dispensing unit of volatilizable substance capable of visible determination of its extent of use involving a variably-located weight means associated with a sighting means.

The volatilizable substance may be a totally volatilizable material suspended in a foam-like material such as polyurethane foam or it may be a volatilizable material suspended in a matrix of nonvolatilizable material such as a silica gel by itself or the silica gel-matrix may be further suspended in a rigid foam such as a polyurethane foam.

The weight as described, supra, may be freely rotatable or the weight may be attached to a vertical support and both the weight and vertical support rotate about the "z" axis as will be more specifically described, supra. As the volatilizable substance evaporates, its density decreases whereas the density of the weight remains constant. Accordingly, the moment of inertia and center of gravity vary as the volatilizable substance evaporates and the weight travels in a downward direction as a result of gravitational attraction for the weight means.

The second embodiment of my invention is a dispensing unit of volatilizable material capable of visible determination of its extent of use and having a variable centroid initially located below the geometric center point of the unit with the variable centroid moving in a substantially downward direction on use of the dispensing unit, comprising:

(1) A freely rotatable vertically disposed substantially planar solid vapor impermeable wall member the rotation of which is gravity induced, said wall member having (i) an enclosing outer circumferential boundary having an upper boundary arcuate segment and a lower boundary arcuate segment and (ii) two vertically disposed substantially planar outer surfaces located, respectively, in a first "x-y" plane and in a second "x-y" plane parallel to each other and rotatable about a "z" axis substantially perpendicular to each of said "x-y" planes, said first and second "x-y" planes each having a horizontal "x" axis and a vertical "y" axis;

(2) A shaft means parallel to said "z" axis about which said wall member is capable of rotating;

(3) Located in a third "x-y" plane proximate said lower boundary arcuate segment on and removably affixed to a major portion of at least one of said planar outer surfaces, a laminar matrix of a volatilizable substance included in a nonvolatilizable substance, the medium plane of said laminar matrix being substantially parallel to said first and second "x-y" plane;

(4) Located in a fourth "x-y" plane proximate said upper boundary arcuate segment on and permanently affixed to a minor portion of at least one of said planar outer surfaces a substantially solid visible weight means having a centroid initially located in the proximity of said vertical "y" axis, above the location of said shaft means and at a height above ground greater than the height above ground of the centroid of said laminar matrix;

(5) Associated with said wall member, a fixed sighting means comprising a window means located in a fifth "x-y" plane parallel to said first and second "x-y" planes, perpendicular to said "z" axis and facing said visible weight means, said sighting means having a line of vision through said window in a direction from said window means to at least one given location of said weight means, each line of vision being substantially parallel to said "z" axis whereby as the volatilizable substance evaporates the weight means together with the wall member angularly rotates in said "x-y" plane about said "z" axis leaving its initial position $(x_o, y_o, z_o)$ at the first upper "y" axis location and finally coming to rest at a second lower "y" axis location $(x_f, y_f, z_o)$ which is visibly detectable from said window means, the angular velocity of said weight means together with said wall member being at least in part a function of the rate of elimination from said unit of said volatilizable substance.

However, the dispensing unit of volatilizable substance of my invention does not need to have its weight means fixedly attached or permanently attached to any vertical supports. Thus, as shown in FIGS. 16, 16-A, 17 and 18 the weight means can be freely rotatable (unlike the article shown in FIGS. 1, 21 and 22).

Accordingly, another embodiment of the dispensing unit of volatilizable substance capable of visible determination of its extent of use of my invention comprises:

(1) A fixed vertically disposed substantially planar solid vapor impermeable wall member, said wall member having (i) an enclosing outer circumferential boundary having a first upper boundary arcuate segment and a first lower boundary arcuate segment; (ii) two vertically disposed substantially planar outer surfaces located, respectively, in a first "x-y" plane and in a second "x-y" plane being parallel to each other, said first and second "x-y" planes each having a horizontal "x" and a vertical "y" axis, each of said "x" axis and said "y" axis being perpendicular to a "z" axis; and (iii) a nonbroken vapor impermeable side wall protruding from and contiguous with the entirety of said circumferential boundary extending in a direction substantially parallel to said "z" axis, having a first upper arcuate segment and a second lower arcuate segment;

(2) A cylindrically shaped shaft means having a shaft wall parallel to said "z" axis having a first upper surface segment and a first lower surface surface segment;

(3) Located in a third "x-y" plane proximate said first lower boundary arcuate segment and said second lower arcuate segment on and removably affixed to a major portion of at least one of said planar outer surfaces and a major portion of said second lower arcuate segment, a laminar matrix of a volatilizable substance included in a nonvolatilizable substance (e.g., a perfume material or an insect repellent such as 1-nonen-3-ol suspended in a matrix of silica gel), the medium plane of said laminar matrix being substantially parallel to said first and second "x-y" planes, said matrix having a second upper surface segment parallel to said "z" axis and perpendicular to each of said "x-y" planes and a second lower surface segment parallel to said "z" axis and perpendicular to each of said "x-y" planes, and initially being contiguous with said first lower segment surface;

(4) Located in said third "x-y" plane initially proximate said first upper boundary arcuate segment and said second upper arcuate segment and initially having a major portion of its lower surface contiguous with said second upper surface segment of said matrix a substantially solid, visible, freely rotatable weight means having a centroid initially located in the proximity of said vertical "y" axis above the location of said shaft means and at a height above ground greater than the height above ground of the centroid of said laminar matrix;

(5) Associated with said visible weight means, a fixed sighting means comprising a window means located in a fourth "x-y" plane parallel to said first and second "x-y" planes, perpendicular to said "z" axis and facing said visible weight means, said sighting means having a line of vision through said window means in a direction from said window means to at least one given location of said weight means, said line of vision being substantially parallel to said "z" axis whereby as the volatilizable substance evaporates, the weight means angularly rotates in said third "x-y" plane above said "z" axis leaving its initial position at the first upper "y" axis location $(x_o, y_o, z_o)$ and finally coming to rest at a second lower "y" axis location $(x_f, y_f, z_o)$ which is visibly detectable from said window means, the angular velocity of said weight means being at least in part a function of the rate of elimination from said unit of said volatilizable substance.

Furthermore, the dispensing unit of volatilizable substance capable of visible determination of its extent of use of my invention need not have an actual central or eccentric shaft means, but instead, may rotate using outer bearings as shown in FIGS. 34, 35 and 36 described in detail, infra.

Accordingly, yet another embodiment of my invention for the dispensing unit of volatilizable substance capable of visible determination of its extent of use comprises:

(1) A freely rotatable vertically disposed solid impermeable first wall member, said first wall member having (i) an enclosing first outer circumferential boundary having a first upper boundary arcuate segment and a first lower boundary arcuate segment; (ii) two vertically disposed substantially planar outer surfaces enclosed by said first circumferential boundary and located, respectively, in a first "x-y" plane and in a second "x-y" plane, said first and second "x-y" planes being substantially parallel to each other, said first and second "x-y" planes each having a horizontal "x" axis and a vertical "y" axis, each of said "x" axis and said "y" axis being perpendicular to said "z" axis and (iii) an unbroken vapor impermeable first side wall protruding from and contiguous with the entirety of said first circumferential boundary of said first wall member, extending in a direction substantially parallel to said "z" axis and having a second upper arcuate segment and a second lower arcuate segment;

(2) Proximate to, "x-y" planarly parallel to, "z"-coaxial with and spaced from said first wall member a fixed vertically disposed substantially solid impermeable second wall member, said second wall member having (i) an enclosing second outer circumferential boundary circumscribing the enclosing first outer circumferential boundary of said first wall member; (ii) two vertically disposed substantially planar outer surfaces enclosed by said circumferential boundary located, respectively, in a third "x-y" plane and in a fourth "x-y" plane, said first, second, third and fourth "x-y" planes being substantially parallel to one another, said third and fourth "x-y" planes each having a horizontal "x" axis and a vertical "y" axis, each of said "x" axes and said "y" axes being perpendicular to said "z" axis and (iii) a second non-broken vapor impermeable side wall protruding from and contiguous with the entirety of said second circumferential boundary extending in a direction substantially parallel to said "z" axis and circumscribing said first side wall of said first wall member;

(3) Fixedly positioned revolvable bearing means located between said first side wall and said second side wall enabling said first wall member to freely rotate in its "x-y" plane about said "z" axis within the confines of the second side wall of the second wall member;

(4) Located in a fifth "x-y" plane proximate said first lower boundary arcuate segment and said lower arcuate segment on and removably affixed to a major portion of at least one of said planar outer surfaces of said wall member and a major portion of said second lower arcuate segment of said first side wall of said first wall member, a laminar matrix of a volatilizable substance included in a non-volatilizable substance (e.g., a perfumery material in a silica gel matrix), the median "x-y" plane of said laminar plane of said laminar matrix being substantially parallel to said first, second, third and fourth "x-y" planes;

(5) Located in a sixth "x-y" plane proximate said upper boundary arcuate segment of said first wall member on and permanently affixed to a minor portion of at least one of said planar outer surfaces of said first wall member, substantially solid visible weight means having its centroid initially located in the proximity of said vertical "y" axis above the location of said "z" axis and at a height above ground greater than the height above ground of the centroid of the said laminar matrix;

(6) Associated with said first wall member, a fixed sighting means comprising a window means located in a seventh "x-y" plane parallel to said first, second, third, fourth, fifth and sixth "x-y" planes and perpendicular to said "z" axis, said sighting means having a line of vision through said window means in a direction from said window means to at least one given location of said weight means, said line of vision being substantially parallel to said "z" axis whereby as the volatilizable substance evaporates, the weight means angularly rotates in said sixth "x-y" plane about said "z" axis leaving its initial position ($x_o$, $y_o$, $z_o$) at the first upper "y" axis location and finally coming to rest at a second lower "y" axis location ($x_f$, $y_f$, $z_o$) which is visibly detectable from said window means, the angular velocity of said weight means being at least in part a function of the rate of elimination from said unit of said volatilizable substance.

Mathematical expressions which can be used to formulate computerized designs of the dispensing unit of volatilizable substance of my invention and which are also useful in further defining my invention are as follows:

MOMENTUM BALANCE:

$$[\tfrac{1}{2}(m_1 + m_3 + \int \rho_2 dV_2 + \int V_2 d\rho_2) R^2] \frac{d\mu}{d\theta} = L_1 + L_2$$

TORQUE BALANCE:

$$\tfrac{1}{2}(m_1 + m_3 + \int \rho_2 dV_2 + \int v_2 d\rho_2) R^2 \left(\frac{d^2\mu}{d\theta^2}\right) = \tau_1 + \tau_2$$

wherein $L_1$ represents the momentum of the weight means and $L_2$ represents the momentum of the volatilizable substance which is variable in volume, weight and density. Thus, $L_1$ is defined, thusly:

$$L_1 = m_1 \sqrt{x_1^2 + y_1^2} \left(\frac{d\mu}{d\theta}\right) +$$

$$\left\{ \frac{2 m_1 \mu \left[ x_1 \frac{dx_1}{d\theta} + y_1 \frac{dy_1}{d\theta} \right]}{\sqrt{x_1^2 + y_1^2}} \right\}$$

and $L_2$ is defined, thusly:

$$L_2 = [\int \rho_2 dV_2 + \int V_2 d\rho_2] \sqrt{x_2^2 + y_2^2 + z_2^2} \left(\frac{d\mu}{d\theta}\right) +$$

$$\frac{2[\int \rho_2 dV_2 + \int V_2 d\rho_2]\mu \left[ x_2 \frac{dx_2}{d\theta} + y_2 \frac{dy_2}{d\theta} + z_2 \frac{dz_2}{dv} \right]}{\sqrt{x_2^2 + y_2^2 + z_2^2}}$$

By the same token $\tau$ is the torque of the weight means defined, thusly:

$$\tau_1 = (m_1 g) \sqrt{x_1^2 + y_1^2}$$

and $\tau_2$ is the torque of the volatilizable substance defined, thusly:

$$\tau_2 = [\int \rho_2 dV_2 + \int V_2 d\rho_2]g \sqrt{x_2^2 + y_2^2 + z_2^2}$$

wherein $m_1$ is the mass of the weight means; $m_2$ represents the variable mass of the volatilizable substance; and $m_3$ represents the mass of the support means for both the weight means and the volatilizable substance. By the same token $\rho_1$ is the density of the weight means and $\rho_2$ is the variable density of the volatilizable substance.

$x_1$ Is the horizontal distance from the centroid of the weight means to the "z" axis; $y_1$ is the vertical distance from the centroid of the weight means to the "z" axis; $x_2$ is the horizontal distance from the centroid of the volatilizable substance to the "z" axis; $y_2$ is the vertical distance from the centroid of the volatilizable substance to the "z" axis; $z_2$ is the "z" distance from the centroid of the volatilizable substance to the "x-y" plane of the volatilizable substance (that is, the median plane);

"$\theta$"

is time and

"$\mu$"

represents the angle through which the weight means and volatilizable substance rotate; lower "g" is gravitational acceleration; $V_2$ is the variable volume of the volatilizable substance.

Furthermore, the "equation of state" may be written, thusly:

$$\left\{ \left(\frac{d\mu}{d\theta}\right) = K\left(\frac{dm_2}{d\theta}\right) = K\left[\frac{d(\rho_2 V_2)}{d\theta}\right] = K\left[\rho_2 \frac{dV_2}{d\theta} + V_2 \frac{d\rho_2}{d\theta}\right] \right\}$$

wherein "K" represents a constant.

BRIEF DESCRIPTION OF THE DRAWINGS

FIG. 8 is the rear view of the article of FIG. 1 at the point of commencement of operation, with the centroid of the weight means at a location on the "y" axis at a position, $(0, y_i, z_i)$.

FIG. 8A is the rear view of that element of the article of FIG. 1 containing the weight means and the volatilizable substance at that point in time of the start of operation of the article.

FIG. 9 is a rear view of the article of FIG. 1 when in operation.

FIG. 9A is a rear view of that element of the article of FIG. 1 when said article is in operation which element contains the weight means and the volatilizable substance, showing the centroid of the weight means moved to a new position, $(x, y, z)$ with the matrix containing the volatilizable substance partially reduced in volume and density.

FIG. 10 is the rear view of the article of FIG. 1 when completely used and when the volatilizable substance is fully expended with the location of the weight means at a point $(o, -y_f, z_f)$ FIG. 10A is the rear view of that element of the article of FIG. 1 which previously contained volatilizable substance and containing the weight means when the article is fully expended and no longer contains any volatilizable substance.

FIG. 11 is the rear view of another embodiment of the element of the article of FIG. 1 containing the weight means and the volatilizable substance wherein the volatilizable substance is located in a gel which is suspended in a macroporous foam, e.g., a large pore polyurethane foam, when the article of my invention is at its initial point of use.

FIG. 11A is the rear view of the element of FIG. 11 when the article of FIG. 1 is in use and the centroid of the weight means is at $(x, y, o)$.

FIG. 11B is the rear view of the element of FIG. 11 when the volatilizable material in the holding matrix thereof is fully expended and the weight means is at a location $(o, -y_f, o)$.

FIG. 12 is the rear view of an element containing a freely rotatable weight means and volatilizable substance which element is a part of the article illustrated in FIGS. 16, 16A, 17 and 18 and which element is shown in exploded, perspective view in FIG. 18, when the article is at that point of initial use (at $\theta$.

FIG. 12A is the rear view of the element of FIG. 12 after use of the article of FIGS. 16, 16A and 17 has commenced, showing the freely rotatable weight means having its centroid at location $(x, y, z)$.

FIG. 12B is a rear view of the element of FIG. 12 after the volatilizable substance contained in the element has been fully expended showing the centroid of the freely rotatable weight means at location $(o, -y_f, z_f)$.

FIG. 13 is a cut-away side elevation view of another embodiment of the dispensing unit of volatilizable substance capable of visible determination of its extent of use of my invention in exploded fashion wherein the weight means and volatilizable substance-containing matrix are together on a freely rotatable element within the unit.

FIG. 14 is the front view of the article of FIG. 13 looking in the direction of the sighting means with the outer element of said article being partially cut-away to shown holes through which the volatilizable substance, e.g., air freshener, deodorant, perfume, insect repellent or insect attractant escapes.

FIG. 15 is a cut-away side elevation view of the article of FIG. 14.

FIG. 16 is the front view of another embodiment of the dispensing unit of volatilizable substance capable of visible determination of its extent of use of my invention with the freely rotatable weight means looking at the article in the direction of the sighting means at that point in time when said article has not yet been put into use.

FIG. 16A is the front view of the article of FIG. 16 at that point in time when the volatilizable substance contained therein is completely expended.

FIG. 17 is a cut-away side elevation view of the article of FIG. 16 at that point in time when use of the article has not yet commenced.

FIG. 18 is a perspective view, in exploded fashion, of that element of the article of FIG. 16 housing the freely rotatable weight means and also housing the matrix containing the volatilizable substance.

FIG. 23 is a perspective view of an element freely rotatable on a shaft having a weight means and a volatilizable substance supported on a vertically disposed rotatable disk freely rotatable about a shaft; and useful with a sighting means (not shown).

FIG. 23A is a front view of the element of FIG. 23.

FIG. 24 is another embodiment of an element of the dispensing unit of volatilizable substance capable of visible determination of its extent of use where the weight means is in the form of a cylindrical sector.

FIG. 24A is the front view of the element of FIG. 23.

FIG. 25 is another embodiment of an element of the dispensing unit of volatilizable substance capable of visible determination of its extent of use where the element is in the shape of a paraboloid and the weight means is an integral part of the paraboloid.

FIG. 25A is a cut-away cross sectional view of the paraboloid element of FIG. 25.

FIG. 26 is another embodiment of an element for use with the dispensing unit of a volatilizable substance capable of visible determination of its extent of use, with the element being in the shape of an elliptical cylinder rotatable about a shaft with the weight means being a secantial section of the elliptical cylinder.

FIG. 26A is a front view of the element of FIG. 26.

FIG. 27 is another embodiment of an element used in conjunction with the dispensing unit of a volatilizable substance capable of visible determination of its extent of use. The element is shown in perspective view with volatilizable substance coated on both sides of a circular planar support which is vertically disposed; and the weight means is a secantial section.

FIG. 28 is a perspective view of another embodiment of the element used in conjunction with the dispensing unit of a volatilizable substance capable of visible determination of its extent of use where the element is in the shape of an eccentric parabolo-elliptical cylinder.

FIG. 28A is a front view of the element of FIG. 28.

FIG. 29 is a perspective view of another embodiment of an element used in conjunction with the dispensing unit of a volatilizable substance capable of visible determination of its extent of use in the shape of an eccentric elliptical cylinder.

FIG. 29A is a front view taken in cross section of the element of FIG. 29.

FIG. 30 is a vertical cross-sectional view of another embodiment of an element used in the dispensing unit of a volatilizable substance capable of visible determination of its extent of use of my invention, having one weight means.

FIG. 31 is a cut-away cross-sectional front view of another embodiment of an element used in conjunction with the dispensing unit of a volatilizable substance capable of visible determination of its extent of use of my invention.

FIG. 32 is a cut-away cross-sectional view of another embodiment of an element having a weight means and a volatilizable substance used in conjunction with the dispensing unit of a volatilizable substance capable of visible determination of its extent of use, having two weight means.

FIG. 33 is a cut-away cross-sectional view of another embodiment of an element having a weight means and a volatilizable substance used in conjunction with the dispensing unit of a volatilizable substance capable of visible determination of its extent of use, having two weight means.

FIG. 34 is the front view of another embodiment of the dispensing unit of volatilizable substance capable of visible determination of its extent of use looking towards the sighting means wherein the element having the weight means and volatilizable substance is capable of freely rotating within a housing with bearing means between the outer housing and the element containing the waiting means and the volatilizable substance.

FIG. 35 is a cut-away elevation view of the dispensing unit of FIG. 34 taken along line 35—35 looking in the direction of the arrows.

FIG. 36 is a cut-away elevation view of the rear of the dispensing unit of FIG. 34 taken along lines 36—36 of FIG. 35 looking in the direction of the arrows.

FIG. 38 is a perspective view of an element in conjunction with the dispensing unit of volatilizable substance capable of visible determination of its extent of use of my invention in the shape of a hemisphere wherein the weight means is set in the matrix of volatilizable substance affixed to a support means and wherein the weight means is in the shape of a frustum of a cylinder, said element being freely rotatable about a shaft.

FIG. 38A is a cut-away side elevation view of the element of FIG. 38.

FIG. 39 is a perspective view of another embodiment of an element useful in conjunction with the dispensing unit of volatilizable substance capable of visible determination of its extent of use, said element being in the shape of an hemi-ellipsoid with the weight means being spherical and being imbedded in a secantial section of a matrix containing volatilizable substance (without showing the sighting means).

FIG. 39A is a cut-away cross-sectional view of the element of FIG. 39.

DETAILED DESCRIPTION OF THE DRAWINGS

Figure 1:
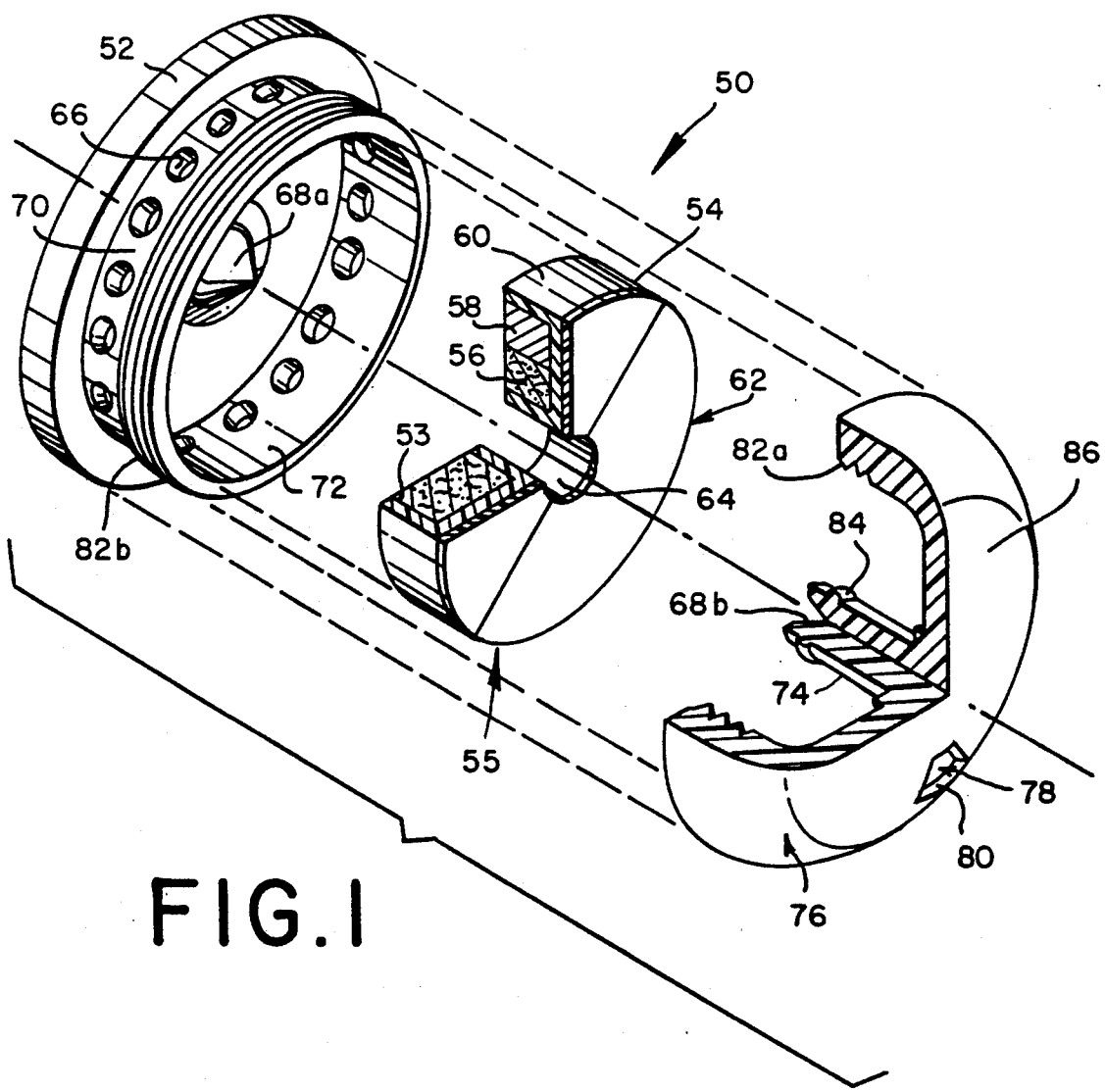
FIG. 1 is a view, in perspective, in schematic form, of an exploded embodiment of a dispensing unit of volatilizable substance capable of visible determination of its extent of use of my invention wherein the volatilizable substance and the weight means rotate on a rotatable support when the article is in use.
Figure 2:
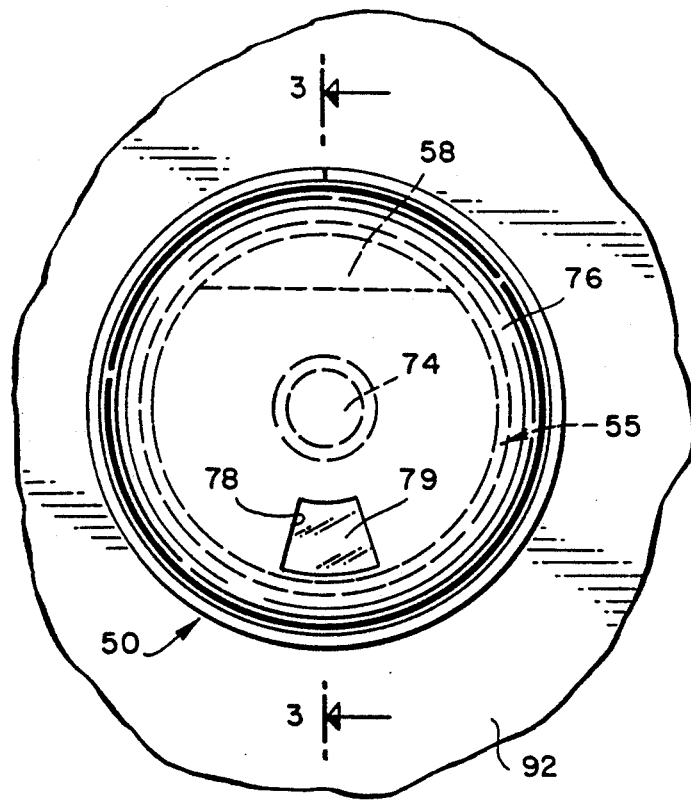
FIG. 2 is a front view of the article of FIG. 1 when observed with a line of sight towards the sighting means.

FIGS. 1, 2, 3, 4, 5, 6, 7, 8, 9, 10, 8A, 9A and 10A illustrate the workings of one embodiment of the dispensing unit of volatilizable substance capable of visible determination of its extent of use. The dispensing unit consists of:

(1) A fixed vertically disposed substantially planar solid vapor impermeable wall member 62 having (i) an enclosing outer circumferential boundary having a first upper boundary arcuate segment and a first lower boundary arcuate segment; (ii) two vertically disposed substantially planar outer surfaces located, respectively, in a first "x-y" plane and in a second "x-y" plane being parallel to each other, said first and second "x-y" planes each having a horizontal "x" axis, 706 (shown in FIG. 19) and a vertical "y" axis, 704 (shown in FIG. 19) each of said "x" axes and said "y" axes being perpendicular to a "z" axis 700 (shown in FIG. 20); and (iii) a non-broken vapor impermeable side wall 60 (shown in FIG. 1) protruding from and contiguous with the entirety of said circumferential boundary extending in a direction substantially parallel to said "x" axis 706 having a first upper arcuate segment area and a second lower arcuate segment;

(2) A cylindrically shaped shaft means 74 having a shaft wall parallel to said "z" axis 700 having a first upper surface segment and a first lower surface segment with the shaft means having a retaining rib 84 capable of holding element or cartridge 55 in a freely rotatable manner;

(3) Located in a third "x-y" plane proximate said first lower boundary arcuate segment and said second lower boundary arcuate segment on and removably affixed to a major portion of at least one of said planar outer surfaces and a major portion of said second lower arcuate segment, a laminar matrix of a volatilizable substance 56 included in a non-volatilizable substance (e.g., a perfuming material in a gel), the medium plane of said laminar or matrix 56 being substantially parallel to said first and second "x-y" planes, said matrix 56 having a second upper surface segment parallel to said "z" axis 700 and perpendicular to each of said "x-y" planes and a second lower surface segment parallel to said "z" axis 700 and perpendicular to each of said "x-y" planes and initially being contiguous with said first lower segment surface;

(4) Located in said third "x-y" plane initially proximate said first upper boundary arcuate segment and said second upper arcuate segment and initially having a major portion of its lower surface contiguous with the second upper surface segment of said matrix, a substantially solid visible weight means 58 having a centroid 658a (shown in FIG. 19) initially located in the proximity of said vertical "y" axis 704 (shown in FIG. 19) above the location of said shaft means 74 and at a height above ground greater than the height above ground of the centroid of the laminar matrix (the matrix containing the volatilizable material) 56;

(5) Associated with the visible weight means 58, a fixed sighting means (e.g., a window 78 having window wall 80) located in a fourth "x-y" plane parallel to said first and second "x-y" planes perpendicular to said "z" axis 700 (shown in FIGS. 19 and 20) and facing said visible weight means 58, said sighting means 78 having a line of vision through said window means 78 in a direction from said window means 78 to at least one given location of said weight means 58 said line of vision being substantially parallel to said "z" axis 740 whereby as the volatilizable substance evaporates from the matrix holding it 56 the weight means 58 angularly rotates in said third "x-y" plane above said "z" axis 700 leaving its original position as shown in FIG. 8A at the first upper "y" axis location going through the position during use as shown in FIG. 9A and coming to rest at a second lower "y" axis location as shown in FIG. 10A which is visibly detectable from the window means 78 (for example, by means of color change appearing on disk 62). The angular velocity of the weight means 58 is at least in part a function of the rate of elimination from the unit 50 of the volatilizable substance from the matrix in which it is located 56. The element 55 holding the matrix containing the volatilizable substance 56 and holding the weight means 58 within vertically disposed support 62 and side wall 60 has an inner wall 53 and a hole 64 therethrough which enables the cartridge 55 to be supported on retaining rib 84 of the shaft means 74 which is part of the outer cover 76 within which window 78 having window wall 80 is located. Cover 76 has outer surface 86 in which is located window 78 having window wall 80. Cover 76 supporting cartridge 54 on retaining rib 84 is detachably attached to wall support 52 via screw thread 82A of cover 76 and screw thread 82B of wall support 52. Screw thread 82B of wall support 52 has its location on side wall 70 which has in a portion next to the screw thread a series of apertures 66 through which the volatilizable substance escapes as it is evaporating from the matrix containing the volatilizable substance 56. Side wall 70 has inner wall 72 which has a diameter slightly greater than the diameter of cartridge 55. The shaft means 74 having retaining rib 84 also has a rotation surface 68B which rotates on pen 68A of wall member 52. Overall cartridge 55 freely rotates on shaft means 74 when the dispensing unit is in use and when the dispensing unit is in use apertures 66 are exposed to the outer atmosphere.

Figure 3:
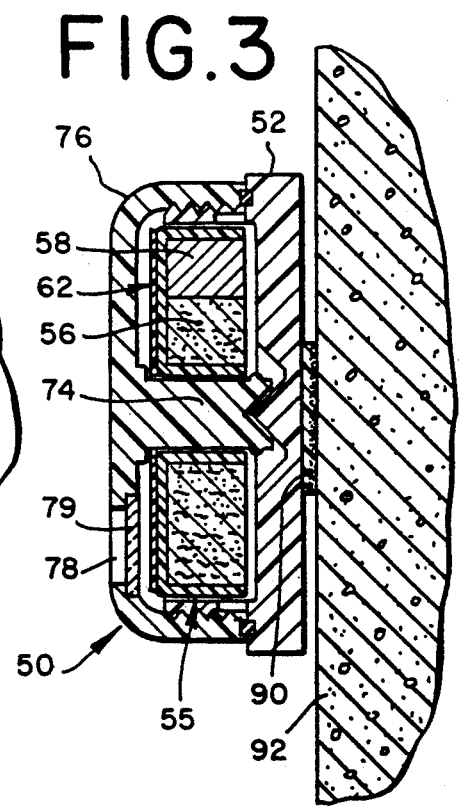
FIG. 3 is a cut-away side elevation view of the article of FIG. 1 taken along line 3—3 of FIG. 2.
Figure 5:
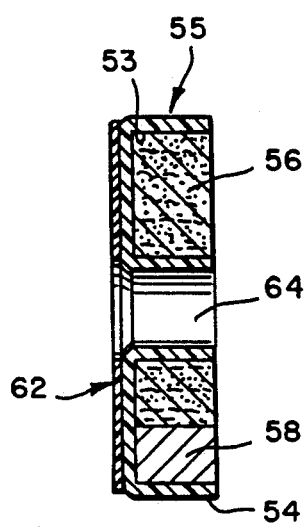
FIG. 5 is a cut-away side elevation view of the element of FIG. 4 taken along line 5—5 looking in the direction of the arrows.
Figure 4:
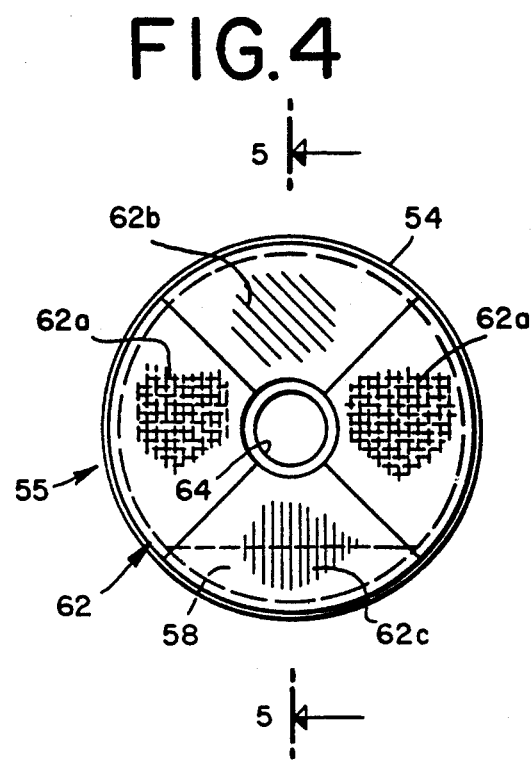
FIG. 4 is a front view of the "indicator" side of the element of the article of FIG. 1 containing the weight means and the volatilizable substance.
Figure 6:
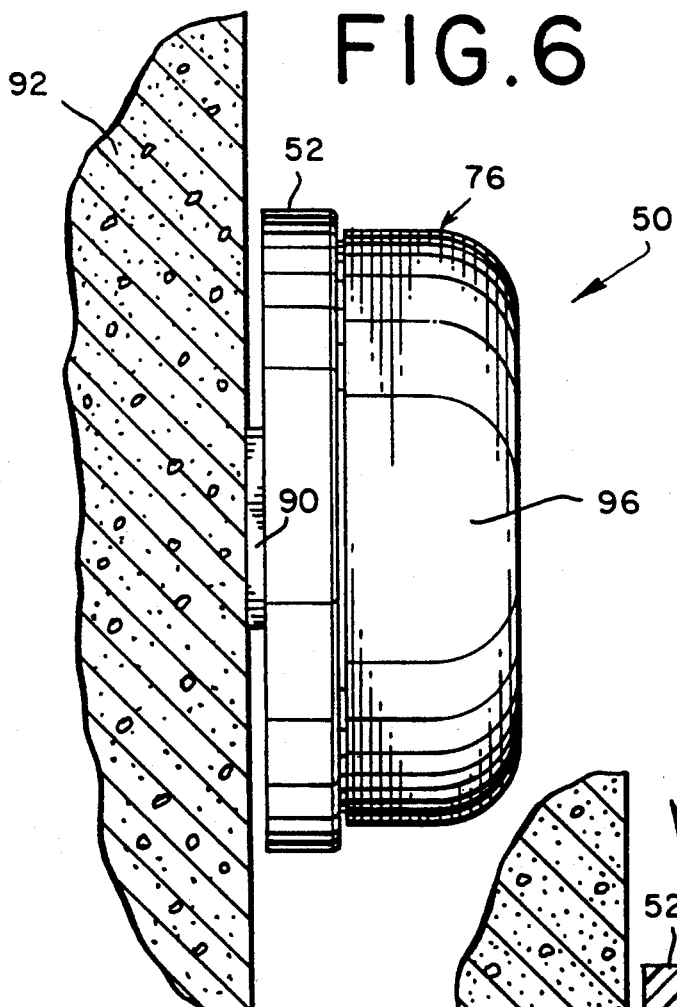
FIG. 6 is a side view of the article of FIG. 1, when closed and not in operation, attached to a wall.

As seen in FIG. 3, the wall member 52 is attached via tape or adhesive 90 to wall 92. Also as seen in FIG. 3, the sighting window 78 has a protective clear screen, e.g., clear glass or polyacrylate 79 through which colored portions of disk 62 may be observed. The various colored portions of disk 62 are shown in FIG. 4 as 62A, 62B and 62C. Thus, for illustrative purposes in FIG. 4, when the volatilizable substance is completely expended, 62C has a distinctive color, e.g., red since weight means 58 is located adjacent window 78 behind glass or plastic screen 79.

Figure 7:
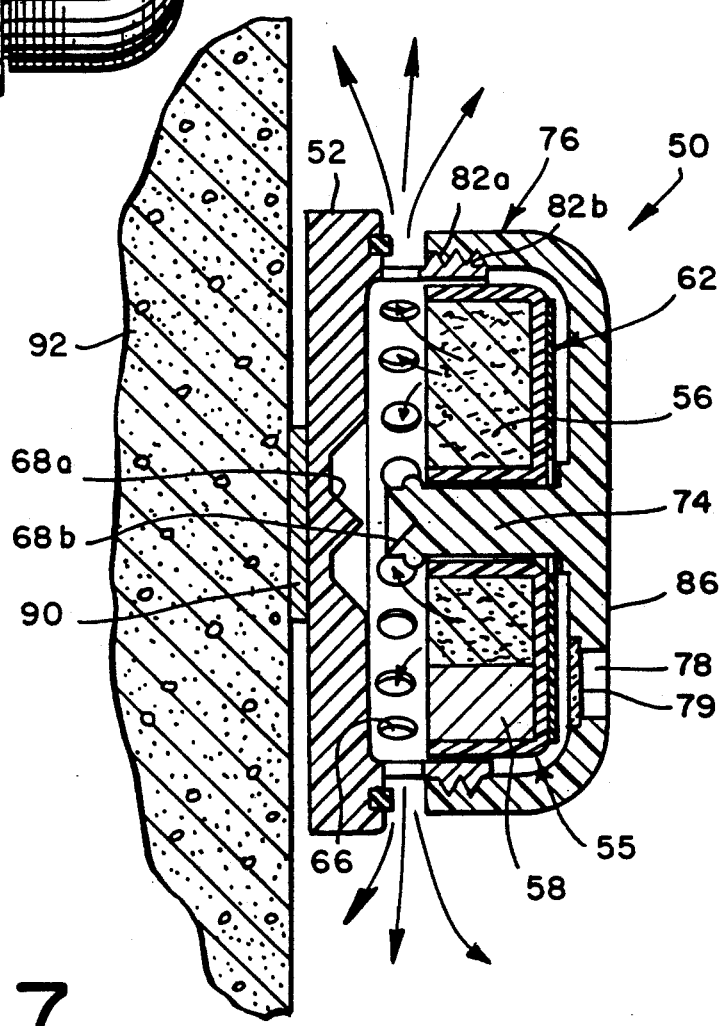
FIG. 7 is a cut-away side elevation view of the article of FIG. 1 when in operation.

During the dispensing of the volatilizable substance, e.g., perfumery material or air freshener into the surrounding environment 94 (as shown in FIG. 7) the weight means 58 rotates as is shown in progressive stages in FIGS. 8, 8A, 9, 9A, 10 and 10A. During the rotation, for example, as is seen in FIG. 9A, the matrix or gel containing the volatilizable substance 56 may retract from the wall of the dispensing unit 53 so that the edge of the matrix achieves an irregular shape as is shown at reference numeral 57 of FIG. 9A. When no volatilizable substance is left, the matrix will have shrunk to a very small volume and this is shown in FIG. 10A using reference numeral 59.

The matrix containing the volatilizable material may also be in the form of a macroporous foam as is shown in FIGS. 11, 11A and 11B where weight means 158 rotates about shaft means 174 as part of element 154. The solid plastic foam, e.g., polyurethane form as shown by reference numeral 356 and the gel containing volatilizable material in the pores of the foam 356 is shown by reference numeral 256. When the volatilizable material is completely expended void spaces exist in the plastic foam 356 as shown by reference numeral 159 in FIG. 11B.

Figure 19:
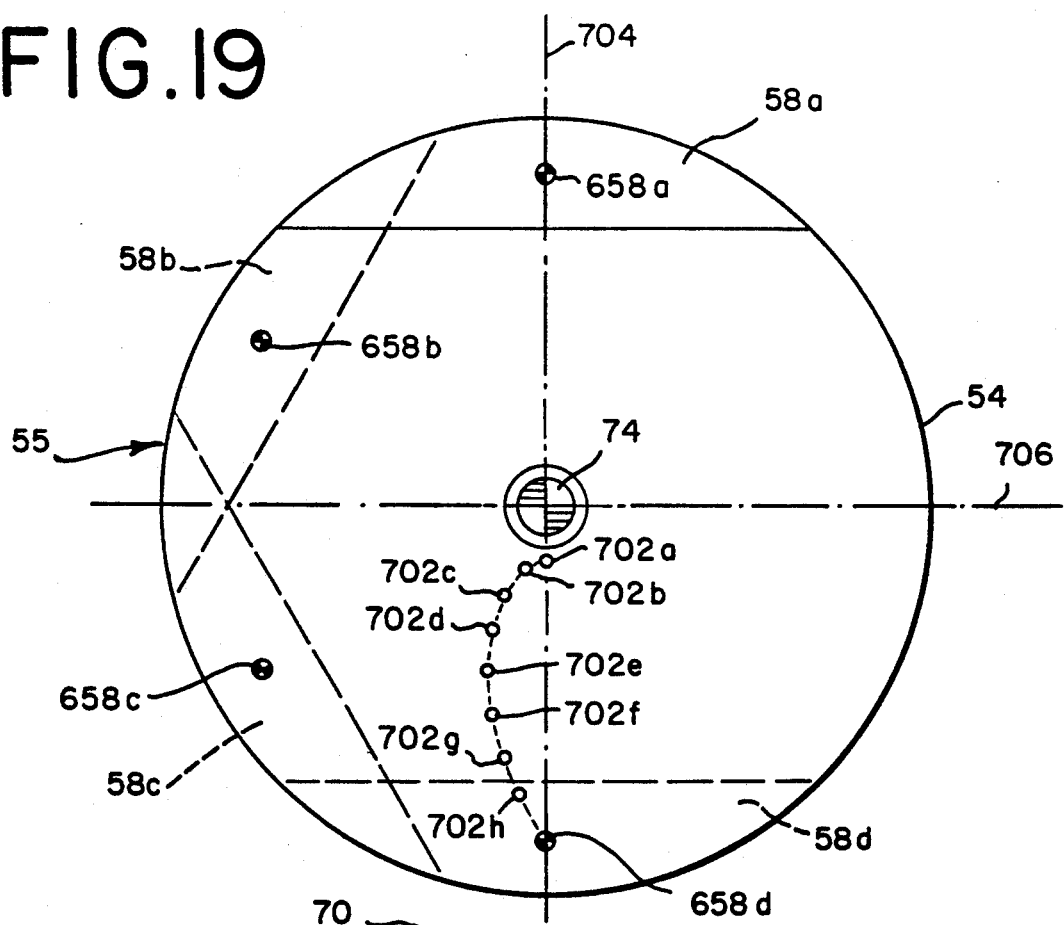
FIG. 19 is a diagram, in graphical form, showing the shifting position of the centroid of the element of the article of FIG. 1 as the article of FIG. 1 is being used; and also showing the shifting position of the weight means of the article of FIG. 1 as the article is being used.
Figure 20:
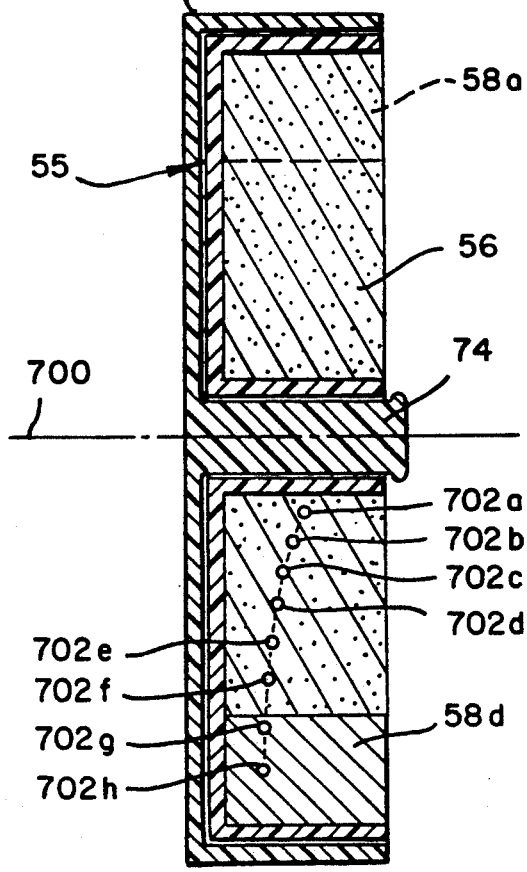
FIG. 20 is a cut-away side elevation view, in graphical representation, of the element of FIG. 19.
Figure 21:
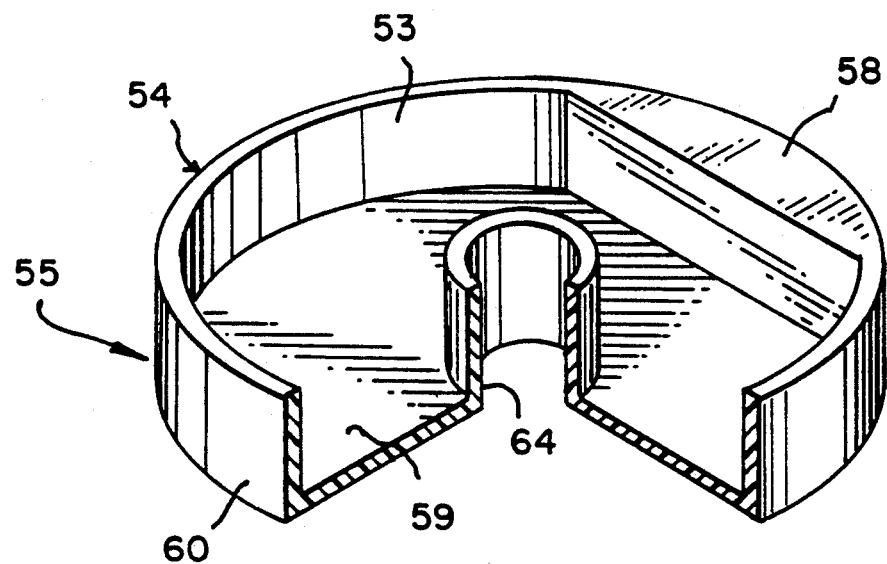
FIG. 21 is a perspective view of the element of the article of FIG. 1, containing the weight means and the volatilizable substance, showing the weight means as an integral part of the element, rotatable with entire element.
Figure 22:
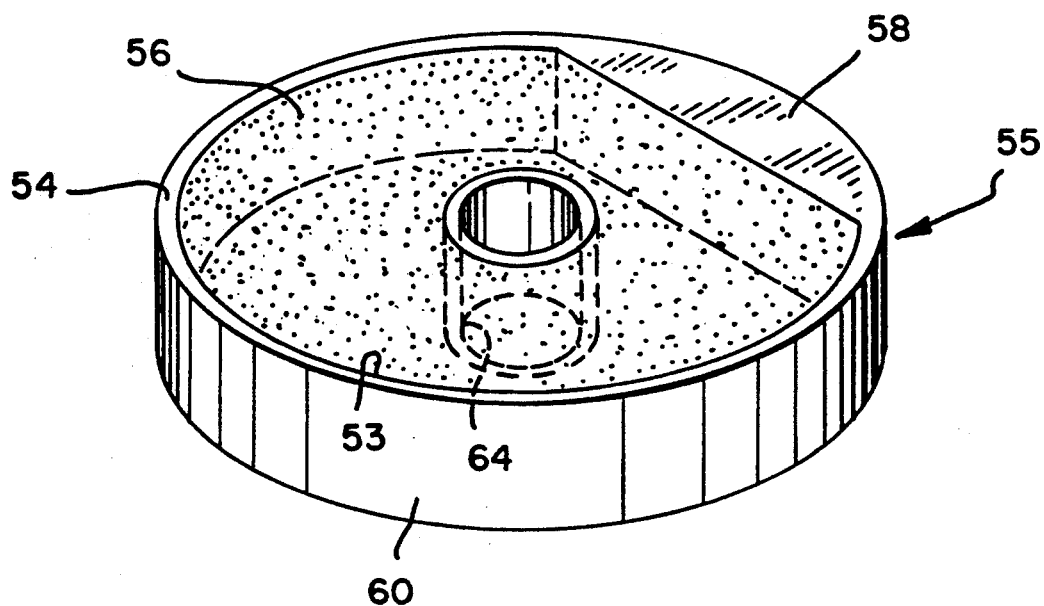
FIG. 22 is a perspective view of the element of FIG. 21, containing a matrix containing the volatilizable substance, a gel.

During the operation of the dispensing unit of volatilizable substance of my invention, the overall centroid will vary in location as shown in FIGS. 19 and 20. Thus, initially prior to use of the dispensing unit of my invention the centroid of the element 55 in FIG. 19 is located at 702a below the shaft means 74; and the centroid of the weight means 58a is shown at 658a. While the dispensing unit is in use, the centroid of the weight means 58a proceeds from location 658a to location 658b to location 658c and finally at the end of its use time to location 658d where the weight means as 58d. At the same time the centroid of the overall element 55 moves from location 702a through location 702b, location 702c, location 702d, location 702e, location 702f, location 702g, location 702h and finally to location 658d where it is substantially identical to the centroid of the weight means 58d.

On the other hand, the weight means instead of being fixedly attached to disk 52 as shown in FIG. 1, can be freely rotatable as shown in FIGS. 12, 12a, 12b, 16, 16a, 17 and 18.

FIGS. 16, 17 and 18 show a dispensing unit of volatilizable substance in a matrix 556 capable of visible determination of its extent of use and having a variable centroid initially located below the geometric center point of the unit with the variable centroid moving in a substantially downward direction on use of the dispensing unit consisting of:

(1) A fixed vertically disposed substantially planar solid vapor impermeable wall member having (i) an enclosing outer circumferential boundary having a first upper boundary arcuate segment and a first lower boundary arcuate segment (ii) two vertically disposed substantially planar outer surfaces located, respectively, in a first "x-y" and in a second "x-y" plane being parallel to each other, said first and second "x-y" planes each having a horizontal "x" axis and a vertical "y" axis. Each of said "x" axes and said "y" axes being perpendicular to a "z" axis which is the center of shaft 574 and (iii) a nonbroken vapor impermeable side wall 560 protruding from and contiguous with the entirety of the circumferential boundary extending in a direction substantially parallel to the "z" axis having a first upper arcuate segment and a second lower arcuate segment;

(2) A shaft means 574 parallel to the "z" axis which is cylindrically shaped;

(3) Located in a third "x-y" plane proximate said first lower boundary arcuate segment and said second lower arcuate segment on and removably affixed to a major portion of at least one of said planar outer surfaces and a major portion of said second lower arcuate segment, a laminar matrix of a volatilizable substance, e.g., a perfume composition, an air freshener or an insect repellent 556 included in a nonvolatilizable substance, e.g., a gel, the median plane of said laminar matrix 556 being substantially parallel to said first and second "x-y" planes;

(4) Located in a third "x-y" plane initially proximate said first upper boundary arcuate segment and said second upper arcuate segment and initially having a major portion of its lower portion contiguous with the second upper surface segment of said matrix 556, a substantially solid, visible, freely rotatable weight means 558 having a centroid initially located in the proximity of said vertical "y" axis above the location of said shaft means 574 and at a height above ground greater than the height above ground of the centroid of said laminar matrix 556;

(5) Associated with said visible weight means 558, a fixed sighting means comprising a window means 578a, 578b, 578c, and 578d located in a fourth "x-y" plane parallel to said first and second "x-y" planes perpendicular to aid "z" axis and facing said visible weight means 558, said sighting means 578a, 578b, 578c and 578d having a line of vision through said window means in a direction from said window means 578a, 578b, 578c and 578d to at least one given location of said weight means (and in the case of FIGS. 16, 16a and 17, four locations) whereby as the volatilizable substance evaporates from the matrix 556 the weight means 558 angularly rotates in said third "x-y" plane above said "z" axis leaving its initial position at the first upper "y" axis location (in the proximitey of windows 578a and 578d and finally coming to rest at a second lower "y" axis location (between 578c and 578b which is visibly detectable from said window means 578a, 578a and 578d, the angular velocity of said weight means 558 being at least in part a function of the rate of elimination from said unit or cartridge 555 of the volatilizable substance into the environment 594. Thus, as volatilizable substance evaporates from the matrix 556 when the unit is in operation the volatilizable substance evaporates through apertures 556 located in cover 576 into the environment 594 while the unit as shown in FIGS. 16, 16a and 17 is attached via tape or adhesive 590 to wall 592. Base 552 holds in place cover 576 having outer surface 586 sighting means 578a, 578b, 578c and 578d are located in cover 576 located in base 552 are vents 557 in order to enable equilibration as vapor leaves through apertures 566; the vents being given reference numeral 557. Shaft 574 is fixed to pin 568 in view of the fact that weight means 558 rotates but container 554 does not rotate during use (as opposed to the embodiment shown in FIG. 1) holding in place weight means 558 (in the confines of its own "x-y" plane is disk 579 which is located between container 554 and outer cover 576. Disk 579 also keeps in place any flowable matrix material which might be present in matrix 556.

The rotatable weight means 558 of FIGS. 16 and 16a is also shown in operation in FIGS. 12, 12a and 12b as reference numeral 258. As the volatilizable material is expended from matrix 256 (shown in FIG. 12a) weight means 258 rotates about shaft 274 until it comes to rest as is shown in FIG. 12b leaving voids 259 as a result of the elimination of volatilizable substance from matrix 256. Also the edge of matrix 256 may contract from the edges of wall 254 as shown in FIG. 12a where the edge of the gel or matrix is shown by reference numeral 157.

FIGS. 13, 14 and 15 show another embodiment of the dispensing unit of my invention wherein location of weight means 458 is observed through sighting means 478 in cover 476 as volatilizable substance is emitted through apertures 466 from space 496 into the environment 494 through porous surface 486, the weight means 458 rotates about shaft means 474. The shaft means 474 has protrusions 484 on which container 454 rotates. The protrusions of shaft means 474, that is, protrusions 484 rest on pin 468 which is part of the holey wall 470. As the volatilizable substance is emitted from the matrix 456 weight means 458 rotates about shaft means 474. Container 454 is held in place by cover 476 located on seat 499 which fits into wall member 452. Wall member 452 is adhered to a wall by means of adhesive 496 and tape 490. The overall unit is indicated by reference numeral 400.

Window means 478 capable of observing any location of weighting means 458 may optionally contain a protective glass or clear plastic 479.

FIGS. 34, 35 and 36 illustrate another embodiment of my invention for a dispensing unit of volatilizable substance capable of visible determination of its extent of use. The unit consists of:

(1) A freely rotatable vertically disposed substantially solid impermeable first wall member. Said first wall member having (i) an enclosing first outer circumferential boundary having a first upper boundary arcuate segment and a first lower boundary arcuate segment (ii) two vertically disposed substantially planar outer surfaces enclosed by said first circumferential boundary and located, respectively, in a first "x-y" plane and in a second "x-y" plane, said first and second "x-y" planes being substantially parallel to each other, said first and second "x-y" planes each having a horizontal "x" axis and a vertical "y" axis each of said "x" axes and said "y" axes being perpendicular to said "z" axes and (iii) an unbroken vapor impermeable first side wall 1102 protruding from and contiguous with the entirety of said first circumferential boundary of said first wall member extending in a direction substantially parallel to said "z" axis and having a second upper arcuate segment and a second lower arcuate segment;

(2) Proximate to, "x-y" planarly parallel to, "z"-coaxial with and spaced from said first wall member a fixed vertically disposed substantially solid impermeable second wall member, said second wall member having (i) an enclosing second outer circumferential boundary 1104; (ii) two vertically disposed substantially planar outer surfaces enclosed by said circumferential boundary located, respectively, in a third "x-y" plane and in a fourth "x-y" plane, said first, second, third and fourth "x-y" planes being substantially parallel to one another, said third and fourth "x-y" planes each having a horizontal "x" axis and a vertical "y" axis, each of said "x" axes and said "y" axes being perpendicular to said "z" axis and (iii) a second nonbroken vapor impermeable side wall protruding from and contiguous with the entirety of said second circumferential boundary extending in a direction substantially parallel to said "z" axis and circumscribing said first side wall of said first wall member;

(3) Fixedly positioned revolvable bearing means 1100 located between said first side wall at 1102 and said second side wall at 1104 enabling said first wall member to freely rotate in its "x-y" plane about said "z" axis within the confines of the second side wall of the second wall member;

(4) Located in a fifth "x-y" plane proximate said first lower boundary arcuate segment and said second lower arcuate segment on and removably affixed to a major portion of at least one of said planar outer surfaces of said first wall member and a major portion of said second lower arcuate segment of said first side wall of said first wall member a laminar matrix 1056 of a volatilizable substance included in a non-volatilizable substance, e.g., a perfumery material or air freshener in a gel, the median "x-y" plane of said laminar plane of said laminar matrix 1056 being substantially parallel to said first, second, third and fourth "x-y" planes;

(5) Located in a sixth "x-y" plane proximate said upper boundary arcuate segment of said first wall member on and permanently affixed to a minor portion of at least one of said planar outer surfaces of said first wall member, substantially solid visible weight means 1058 having its centroid initially located in the proximity of said vertical "y" axis above the location of said "z" axis and at a height above ground greater than the height above ground of the centroid of the said laminar matrix 1056;

(6) Associated with said first wall member a fixed sighting means 1078 (window) having window side 1080 located in a seventh "x-y" plane parallel to said first, second, third, fourth, fifth and sixth "x-y" planes and perpendicular to said "z" axis, said sighting means 1078/1080 having a line of vision through said window means 1078 in a direction from said window means 1078 to at least one given location of said weight means 1058, said line of vision being substantially parallel to said "z" axis whereby as the volatilizable substance evaporates from matrix 1056 the weight means 1058 angularly rotates in said sixth "x-y" plane about said "z" axis leaving its initial position at the first upper "y" axis location and finally coming to rest at a second lower "y" axis location which is visibly detectable from said window means 1078, the angular velocity of said weight means 1058 being at least in part a function of the rate of elimination from said unit 1000 of said volatilizable substance.

The unit 1000 is affixed to wall 1092 by means of tape 1090. A butting tape 1090 is the wall member having affixed thereto cover 1076 having surface 1086 and containing escape holes for the volatilizable substance 1066 and 1166. Between the outer cover 1076 and the inner cartridge 1055 which contains the weight means 1058 and volatilizable substance matrix 1056 are bearing means 1100 which enable cartridge 1055 to rotate as volatilizable substance in matrix 1056 evaporates through microporous cover 1076 (which is part of cartridge 1055) through escape holes 1166 and 1066. Meanwhile, window sighting means 1078 having window side 1080 is also backed by protective glass or plastic 1076 through which the location of the weight means 1058 is ascertained by the viewer. Vents 1057 in the wall member enable the gas within unit 1000 to equilibrate during use of the unit of my invention.

Figure 37:
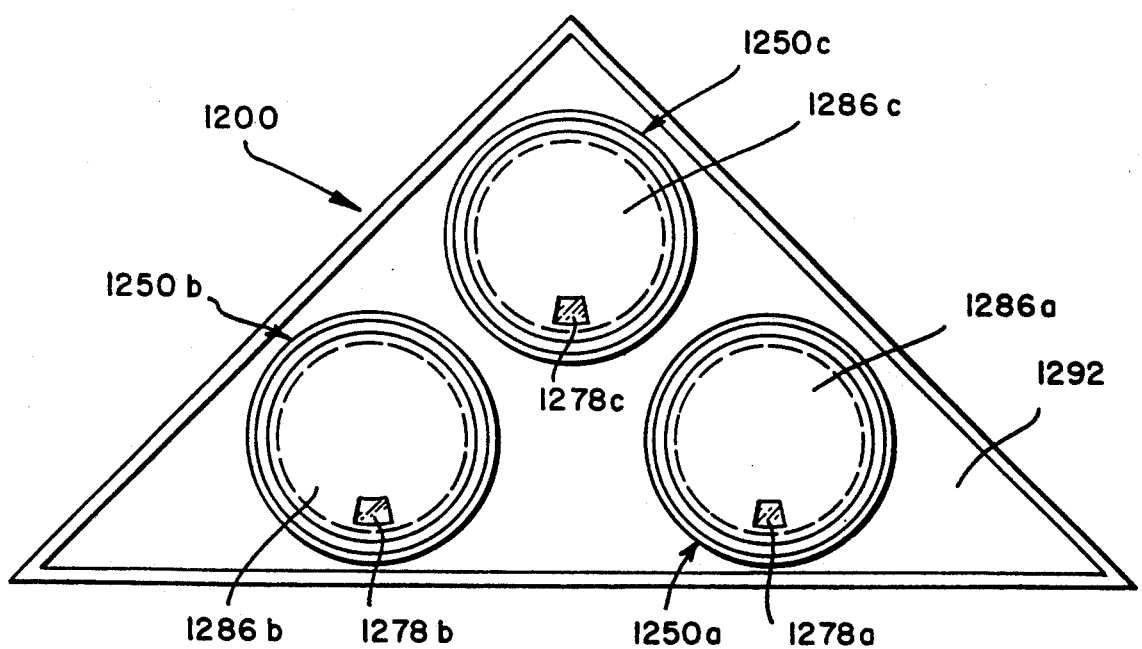
FIG. 37 is a front view of three mounted dispensing units of volatilizable substance(s) each capable of visible determination of its respective extent of use; with each of the units capable of containing different volatilizable materials, e.g., perfumes, insect repellents and deodorants.

Units such as those illustrated in FIGS. 34, 35 and 36 or FIG. 1 or FIG. 16 may be used in conjunction with one another at one geographic location as is illustrated in FIG. 37 wherein unit 1200 contains three units 1250a, 1250b and 1250c located on wall 1292. Unit 1250a has cover 1286a in which is located window means 1278a. Unit 1250c has cover 1286c in which is located window means 1278c. Unit 1250b has cover 1286b in which is located window means 1278b. Each of units 1250a, 1250b and 1250c may contain different volatilizable substances, for example, unit 1250a can contain a contain an insect repellent. As each unit is expended, a viewer can determine that fact by observation through the respective window means, e.g., 1278a, 1278b and/or 1278c thereby enabling replacement of the particular volatilizable substance cartridge in the particular unit involved. In addition, each of units 1250a, 1250b and 1250c can contain, for example, different perfume materials which can be caused to blend with one another as a result of using different cartridges, for example, cartridge 55 of FIG. 1 or cartridge 1055 of FIG. 35.

Elements containing weight means and volatilizable substance may be of various shapes as illustrated in FIGS. 23, 23a, 24, 24a, 25, 25a, 26, 26a. 27. 28, 28a, 29, 29a, 30, 31, 32, 33, 38, 38a, 39 and 39a.

Thus, in referring to FIG. 23, volatilizable substance is located matrix 802 and weight means 808 is contiguous with matrix 802 at surface 809. Both weight means 808 and matrix 802 are contiguous with vertical member 806 at surface 807. The unit 800 rotates about axis 804 as volatilizable substance is emitted from matrix 802.

By the same token, referring to FIG. 24 and 24a, weight means 818 is contiguous with matrix 812 at surfaces 819a and 819b and both weight means 818 and matrix 812 are contiguous with surface 817 on vertical member 816. Unit 810 rotates about axis 814 as volatilizable substance is emitted from matrix 812.

Referring to FIGS. 25 and 25a, matrix 822 is contiguous with weight means 828 at surface 829 and both weight means 828 and matrix 822 are contiguous with vertical member 826 at surface 827. Unit 820 rotates about axis 824 as volatilizable substance is emitted from matrix 822.

By the same token, referring to FIGS. 26 and 26a, volatilizable substance is emitted from matrix 832 on use of unit 830. Volatilizable substance being emitted from matrix 832 causes unit 830 to rotate about axis 834. Matrix 832 is contiguous with weight means 838 at surface 839. Both weight means 838 and matrix 832 are contiguous with vertical member 836 at surface 837.

Referring to FIG. 27, vertical member 846 has two surfaces; surface 847a and 847b. Contiguous with surface 847a is matrix 842a containing volatilizable substance. Contiguous with surface 847b is matrix 842b also containing volatilizable substance. The volatilizable substances of matrix 842a may be the same as or different from the volatilizable substance of matrix 842b. Weight means 848 is contiguous with matrices 842a and 842b at surface 849. As volatilizable substance is eliminated from matrices 842a and 842b the unit 840 rotates around axis 844.

Similarly, referring to the unit 850 of FIG. 28, matrices 852a and 852b have surfaces contiguous with vertical member 856 at surfaces 857a and 857b. The matrices 852a and 852b may contain the same or different volatilizable substances, e.g., one matrix can contain an insect repellent and the other matrix can contain a perfume. Matrices 852a and 852b have surfaces contiguous with weight means 858 at surface 859. As volatilizable substance are emitted from matrices 852a and 852b unit 850 rotates about shaft 854.

By the same token, referring to FIG. 29, matrix 862 containing volatilizable substance has a surface contiguous with the weight means 868 at surface 869. Both weight means 868 and matrix 862 have a surface contiguous with vertical member 866 at surface 867. Unit 860 rotates about shaft 864 as volatilizable substance from matrix 862 is emitted into the atmosphere.

Referring to FIG. 30, matrix 872 containing volatilizable substance has a surface contiguous with weight means 878 at surface 879. As volatilizable substance is emitted from matrix 872 unit 870 rotates about shaft 874.

Referring to FIG. 31, matrix 882 containing volatilizable substance has surfaces contiguous with weight means 888 as indicated by reference numerals 889a and 889b. The advantage of unit 880 is that it can rotate in a clockwise or counterclockwise direction depending on the initial evaporation location of the volatilizable substance from matrix 882. As volatilizable substance is emitted from matrix 882 unit 880 rotates either clockwise or counter-clockwise about axis 884. The center point of symmetrical weight means 888 is at 888x.

In a similar fashion unit 890 illustrated in cross-section area in FIG. 32 has matrix 892 containing volatilizable substance. Matrix 892 has a common surface with weight means 898a at surface 899a. Matrix 892 has a common surface with weight means 898b at surface 899b. When volatilizable substance is emitted from matrix 892 unit 890 rotates about axis 894 either in a clockwise or counter-clockwise direction.

Referring to FIG. 33, FIG. 33 has a volatilizable substance located in matrix 902 surrounded by a magnetic metal casing 954. Magnetically attached to casing 954 at surface 954a is weight means 908a. Magnetically attached to surface 954b is weight means 908b. As volatilizable substance is emitted from matrix 902, unit 900 rotates about axis 904 causing the weight means to come in view of sighting means (not shown).

Referring to dispensing unit 1300 in FIG. 38, having a hemispherical shape, matrix 1302 containing weight means 1308 has a surface 1307 contiguous with vertical member 1306. As volatilizable substance is emitted from matrix 1302 unit 1300 rotates about axis 1304 causing weight means 1308 to be relocated finally at a position directly beneath axis 1304.

Similarly, referring to the hemi-ellipsoid of FIG. 39, matrix 1402 containing volatilizable substance has a surface contiguous with vertical member 1406 at surface 1407. Contained within matrix 1402 is weight member (spherical in shape) 1408. As volatilizable substance is emitted from matrix 1402 unit 1400 rotates about axis 1404 bringing visible weight member 1408 into view of sighting means (not shown).

What is claimed is:

1. A dispensing unit of a volatilizable substance capable of visible determination of its extent of use comprising:
    (1) a vertically positioned rotatable laminar support capable of rotation in a vertical "x-y" plane about a "z" axis, said "z" axis being perpendicular to said "x-y" plane, said support having located thereon and affixed thereto in the proximity of said "x-y" plane:
        (A) a gravity-activated weight permanently affixed to said support; and
        (B) a volatilizable substance,
        said gravity-activated weight being eccentrically located in the proximity of said "x-y" plane with respect to the centroid of the dispensing unit, said support having a variably-located centroid initially positioned proximate the geometric center point of the unit with the centroid moving in a downward direction in said "x-y" plane when the unit is in use; and
    (2) a sighting mechanism means for viewing at least a portion of said laminar support in a direction parallel to said "z" axis and perpendicular to said "x-y" plane, whereby as the volatilizable substance evaporates, the gravity-activated weight angularly rotates about said "z" axis leaving an initial position and finally coming to rest at a resting position when the volatilizable substance is used up and whereby at least the final position of the weight is visibly detectable through said sighting mechanism means.

* * * * *